United States Patent
Goodwin et al.

(10) Patent No.: US 12,018,081 B1
(45) Date of Patent: Jun. 25, 2024

(54) PHOTOCONJUGATION REACTIONS FOR MODIFICATION OF SPECIFIC PROTEINS ON LIVE CELLS

(71) Applicant: The Regents of the University of Colorado, a body, Denver, CO (US)

(72) Inventors: Andrew P. Goodwin, Boulder, CO (US); Jennifer N. Cha, Boulder, CO (US); Shambojit Roy, Boulder, CO (US); Michael D. Brasino, Portland, OR (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 332 days.

(21) Appl. No.: 17/006,635

(22) Filed: Aug. 28, 2020

Related U.S. Application Data

(60) Provisional application No. 62/892,681, filed on Aug. 28, 2019.

(51) Int. Cl.
| | | |
|---|---|---|
| *C07K 16/28* | (2006.01) | |
| *A61K 33/16* | (2006.01) | |
| *A61K 39/00* | (2006.01) | |
| *C12N 9/78* | (2006.01) | |

(52) U.S. Cl.
CPC .......... *C07K 16/2863* (2013.01); *A61K 33/16* (2013.01); *C12N 9/78* (2013.01); *A61K 2039/505* (2013.01); *C12Y 305/04001* (2013.01)

(58) Field of Classification Search
None
See application file for complete search history.

(56) References Cited

U.S. PATENT DOCUMENTS

| | | | |
|---|---|---|---|
| 9,688,739 B2 | 6/2017 | Rosenberg et al. | |
| 2010/0129367 A1* | 5/2010 | Roffler | C12Q 1/34 424/134.1 |
| 2017/0258835 A1* | 9/2017 | Zhao | A61P 9/00 |
| 2018/0243341 A1 | 8/2018 | June et al. | |

OTHER PUBLICATIONS

Brasino et al., J Am Chem Soc, 140:11820-11828, including supplements, 2018.*
Hino et al., Nature Methods, 2(3):201-206, 2005.*
Jung et al., Anal Chem, 81: 936-942, 2009.*
Kamath A. V. (2016). Translational pharmacokinetics and pharmacodynamics of monoclonal antibodies. Drug discovery today. Technologies, 21-22, 75-83. https://doi.org/10.1016/j.ddtec.2016.09.004.
Ryman, J. T., & Meibohm, B. (2017). Pharmacokinetics of Monoclonal Antibodies. CPT: pharmacometrics & systems pharmacology, 6(9), 576-588. https://doi.org/10.1002/psp4.12224.
Baskin JM, Prescher JA, Laughlin ST, Agard NJ, Chang PV, Miller IA, Lo A, Codelli JA, Bertozzi CR. Copper-free click chemistry for dynamic in vivo imaging. Proc Natl Acad Sci U S A. Oct. 23, 2007;104(43): 16793-7. doi: 10.1073/pnas.0707090104. Epub Oct. 17, 2007. PMID: 17942682; PMCID: PMC2040404.
Chang PV, Prescher JA, Sletten EM, Baskin JM, Miller IA, Agard NJ, Lo A, Bertozzi CR. Copper-free click chemistry in living animals. Proc Natl Acad Sci U S A. Feb. 2, 2010;107(5):1821-6. doi: 10.1073/pnas.0911116107. Epub Jan. 14, 2010. PMID: 20080615; PMCID: PMC2836626.
Tamura, T.; Hamachi, I. Chemistry for Covalent Modification of Endogenous/Native Proteins: From Test Tubes to Complex Biological Systems. J. Am. Chem. Soc. 2019, 141 (7), 2782-2799. https://doi.org/10.1021/jacs.8b11747.
Grevys, A., Nilsen, J., Sand, K.M.K et al. A human endothelial cell-based recycling assay for screening of FcRn targeted molecules. Nat Commun 9, 621 (2018). https://doi.org/10.1038/s41467-018-03061-x.
Tzaban S, Massol RH, Yen E, Hamman W, Frank SR, Lapierre LA, Hansen SH, Goldenring JR, Blumberg RS, Lencer WI. The recycling and transcytotic pathways for IgG transport by FcRn are distinct and display an inherent polarity. J Cell Biol. May 18, 2009;185(4):673-84. doi: 10.1083/jcb.200809122. PMID: 19451275; PMCID: PMC2711563.
Hall RS, Fedorov AA, Xu C, Fedorov EV, Almo SC, Raushel FM. Three-dimensional structure and catalytic mechanism of cytosine deaminase. Biochemistry. Jun. 7, 2011;50(22):5077-85. doi: 10.1021/bi200483k. Epub May 12, 2011. PMID: 21545144; PMCID: PMC3107989.
Deckert, P. M., Renner, C., Cohen, L. S., Jungbluth, A., Ritter, G., Bertino, J. R., Old, L. J., & Welt, S. (2003). A33scFv-cytosine deaminase: a recombinant protein construct for antibody-directed enzyme-prodrug therapy. British journal of cancer, 88(6), 937-939. https://doi.org/10.1038/sj.bjc.6600751.

(Continued)

*Primary Examiner* — Marianne P Allen
(74) *Attorney, Agent, or Firm* — Michael M. McGaw; McGaw Law, P.C.

(57) ABSTRACT

A prodrug enzyme covalently photoconjugated to a live cell receptor survives endosomal proteolysis and retains its catalytic activity on the living cell membrane over multiple days. Antibody-directed enzyme prodrug therapy is a promising approach for selective treatment of solid tumors, but methods are needed to preserve enzyme activity on living cell membranes over multiple prodrug dosings. A fusion protein was designed with both an anti-epidermal growth factor receptor (EGFR) affibody and the prodrug enzyme cytosine deaminase, which can convert prodrug 5-fluorocytosine to the anticancer drug 5-fluorouracil. A benzophenone group was added at a site-specific mutation within the affibody portion, and the fusion protein was selectively and irreversibly photoconjugated to EGFR receptors expressed on membranes of live MDA-MB-468 breast cancer cells. Affinity-mediated covalent conjugation of the affibody-enzymes to cell receptors allows for prolonged expression on membranes and retained enzymatic activity without genetic engineering.

16 Claims, 22 Drawing Sheets
Specification includes a Sequence Listing.

(56) References Cited

OTHER PUBLICATIONS

Brasino M, Roy S, Erbse AH, et al. Anti-EGFR Affibodies with Site-Specific Photo-Cross-Linker Incorporation Show Both Directed Target-Specific Photoconjugation and Increased Retention in Tumors. Journal of the American Chemical Society. Sep. 2018; 140(37):11820-11828. DOI: 10.1021/jacs.8b07601. PMID: 30203972; PMCID: PMC6689236.

Sheri D. Mahan, Greg C. Ireton, Catherine Knoeber, Barry L. Stoddard, Margaret E. Black, Random mutagenesis and selection of Escherichia coli cytosine deaminase for cancer gene therapy, Protein Engineering, Design and Selection, vol. 17, Issue 8, Aug. 2004, pp. 625-633, https://doi.org/10.1093/protein/gzh074.

Grunbeck, A., Huber, T., Sachdev, P., & Sakmar, T. P. (2011). Mapping the ligand-binding site on a G protein-coupled receptor (GPCR) using genetically encoded photocrosslinkers. Biochemistry, 50(17), 3411-3413. https://doi.org/10.1021/bi200214r.

Nath, N., Godat, B., Zimprich, C., Dwight, S. J., Corona, C., McDougall, M., & Urh, M. (2016). Homogeneous plate based antibody internalization assay using pH sensor fluorescent dye. Journal of immunological methods, 431, 11-21. https://doi.org/10.1016/j.jim.2016.02.001.

Nordberg, E., Ekerljung, L., Sahlberg, S. H., Carlsson, J., Lennartsson, J., & Glimelius, B. (2010). Effects of an EGFR-binding affibody molecule on intracellular signaling pathways. International journal of oncology, 36(4), 967-972. https://doi.org/10.3892/ijo_00000576.

Fuchita, M., Ardiani, A., Zhao, L., Serve, K., Stoddard, B. L., & Black, M. E. (2009). Bacterial cytosine deaminase mutants created by molecular engineering show improved 5-fluorocytosine-mediated cell killing in vitro and in vivo. Cancer research, 69(11), 4791-4799. https://doi.org/10.1158/0008-5472.CAN-09-0615.

\* cited by examiner

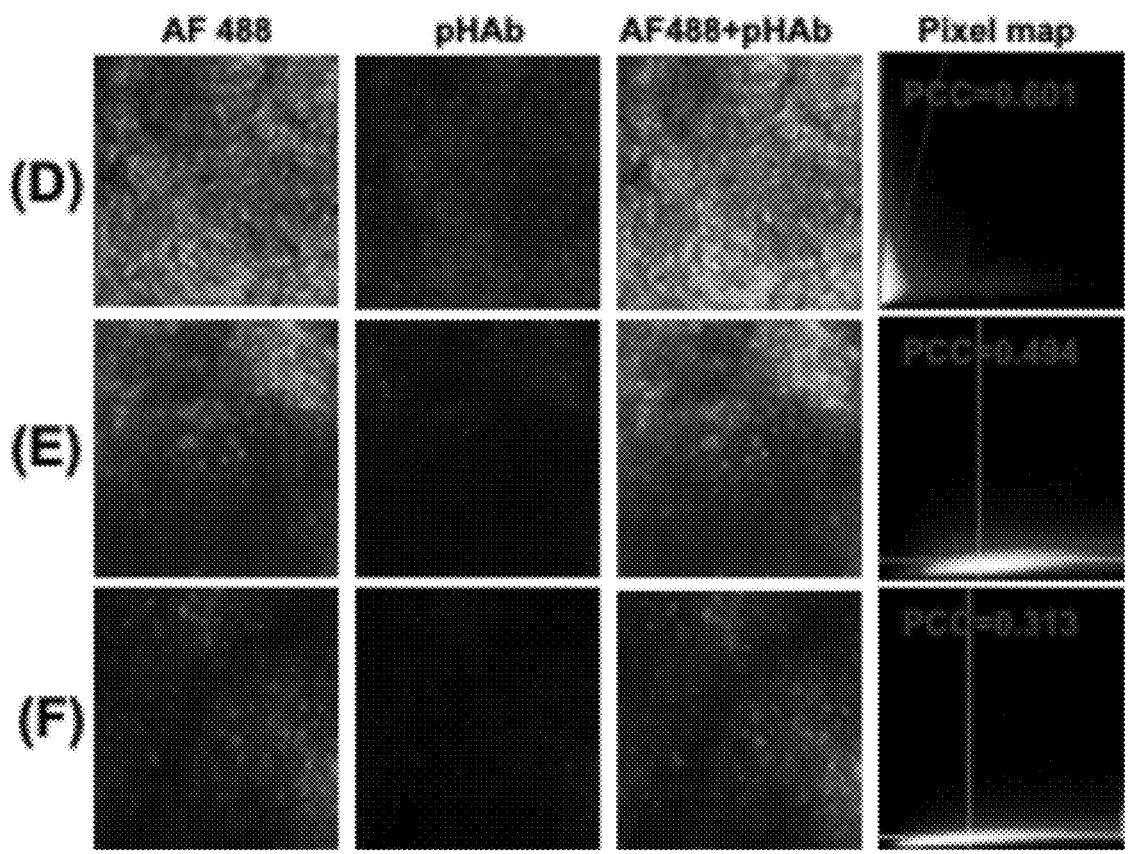
FIG. 3 - continued

SEQUENCE LISTING

<160> NUMBER OF SEQ ID NOS: 2

<210> SEQ ID NO 1
<211> LENGTH: 44
<212> TYPE: DNA
<213> ORGANISM: Artificial Sequence
<220> FEATURE:
<223> OTHER INFORMATION: Forward primer for amplifying CodA gene encoded
      for cytosine deaminase.

<400> SEQUENCE: 1
aagcttggcg gtggctcgaa taacctttac aaacaattat taac                    44

<210> SEQ ID NO 2
<211> LENGTH: 28
<212> TYPE: DNA
<213> ORGANISM: Artificial Sequence
<220> FEATURE:
<223> OTHER INFORMATION: Reverse primer for amplifying the CodA gene
      encoded for cytosine deaminase.

<400> SEQUENCE: 2
tcttcggtag ctaatgtttg cagagctc                                      28

PHOTOCONJUGATION REACTIONS FOR MODIFICATION OF SPECIFIC PROTEINS ON LIVE CELLS

CROSS-REFERENCE TO RELATED APPLICATIONS

This application claims the benefit of U.S. Provisional Application No. 62/892,681, filed Aug. 28, 2019.

STATEMENT OF GOVERNMENT INTEREST

This invention was made with government support under grant number EB020401 awarded by the National Institutes of Health. The government has certain rights in the invention.

REFERENCE TO AN ELECTRONIC SEQUENCE LISTING

The contents of the electronic sequence listing (17-006-635-SEQ-CU-GOODWIN_ST25-v2-22jan.2023.txt; Size: 828 bytes; and Date of Creation: Nov. 21, 2020) is herein incorporated by reference in its entirety.

FIELD OF INVENTION

This invention relates to methods and therapy for cancer treatment. More specifically, this invention relates to compositions and methods for the modification of cell surface proteins using affibody-enzyme fusion polypeptides.

BACKGROUND OF THE INVENTION

Because of the considerable negative side effects of anticancer drugs, many modern chemotherapy approaches seek to localize drug activity to cancerous tissues, for example by biasing drug accumulation through active targeting. Antibody-targeted enzyme prodrug therapy hones a few techniques into one approach. First, an enzyme is conjugated to an antibody so that the conjugate localizes to a solid tumor environment. This step is followed by systemic administration of prodrugs, which are nontoxic molecules that are converted into toxic species by a chemical transformation in the body. By using a bacterial enzyme (e.g. beta-lactamase or cytosine deaminase), prodrug molecules may be converted to drug molecules without a competing background reaction in the human patient. Thus, although the prodrug itself has no inherent selectivity for the cancer, the overabundance of enzyme at the tumor causes selective conversion and toxicity, along with reduced systemic side effects.

However, one of the main roadblocks to clinical acceptance has been the need to administer enzymes multiple times per patient due to loss of activity. Because it is known that cancer cells begin DNA repair within 24 hr. of drug-induced strand breaks, the ability to administer multiple effective prodrug doses is critical for reducing tumor size. Unfortunately, while the presence of the antibody on the enzyme conjugate allows homing to tumor tissue, the antibody also promotes receptor-mediated endocytosis, resulting in catabolic processes that degrade the enzyme. Eventually, repeat dosings become ineffective because the body produces antibodies that clear the antibody-enzyme conjugate before it can reach the tumor.

SUMMARY OF THE INVENTION

A novel prodrug enzyme covalently photo-conjugated to a live cell receptor is shown herein to survive endosomal proteolysis and retain its catalytic activity on the living cell membrane over multiple days. Antibody-directed enzyme prodrug therapy is a promising approach for selective treatment of solid tumors, but methods are needed to preserve enzyme activity on living cell membranes over multiple prodrug dosings. Here, a fusion protein was designed with both an anti-epidermal growth factor receptor (EGFR) affibody and the prodrug enzyme cytosine deaminase, which can convert prodrug 5-fluorocytosine to the anticancer drug 5-fluorouracil. A benzophenone group was added at a site-specific mutation within the affibody portion, and the fusion protein was selectively and irreversibly photo-conjugated to EGFR receptors expressed on membranes of live MDA-MB-468 breast cancer cells. The fusion protein was next labeled with two dyes for tracking uptake: green AlexaFluor 488 and red, pH-sensitive pHAb. Flow cytometry showed that fusion proteins photocrosslinked to EGFR first underwent receptor-mediated endocytosis within 12 hr., followed by recycling back to the cell membrane within 24 hr. These findings were also confirmed by confocal microscopy, which showed similar trends in affibody-enzyme internalization and recycling. Finally, when the affibody-CodA fusion proteins were photocrosslinked to EGFR overexpressed on MDA-MB-468 breast cancer cells, prodrug conversion was found even 48 hr. post-incubation without any apparent decrease in cell killing, while without photocrosslinking no cell killing was observed 8 hr. post-incubation. These studies show that affinity-mediated covalent conjugation of the affibody-enzymes to cell receptors allows for prolonged expression on membranes and retained enzymatic activity without genetic engineering.

In a first aspect the present invention provides a fusion protein comprising an anti-epidermal growth factor receptor (EGFR) affibody having a benzophenone group and a prodrug enzyme. In certain embodiments the prodrug enzyme is cytosine deaminase. In further embodiments the affibody has a conjugated benzophenone group.

In a second aspect the present invention provides an anti-cell surface receptor affibody having a conjugated benzophenone group. In certain embodiments the affibody has a sequence mutation to add a cysteine residue to facilitate conjugation with benzophenone (BP). In certain embodiments the affibody is a fusion protein.

In a third aspect the present invention provides a fusion protein comprising an anti-transmembrane receptor affibody having a conjugated benzophenone group and a prodrug enzyme.

In a fourth aspect the present invention provides a fusion protein comprising an anti-epidermal growth factor receptor (EGFR) affibody having a benzophenone group and a prodrug enzyme.

In a fifth aspect the present invention provides a fusion protein comprising an anti-epidermal growth factor receptor (EGFR) affibody and cytosine deaminase. In certain embodiments the affibody has a affibody of the fifth aspect has a conjugated benzophenone group.

In a sixth aspect the present invention provides a method of treating a disease in a subject. The method according to the sixth aspect can include the steps of contacting a cell with a fusion protein comprising an anti-cell surface receptor affibody having a conjugated benzophenone group fused to a prodrug enzyme and photoconjugating the fusion protein to the surface of the cell. In certain embodiments the method of treating a disease in a subject according to the sixth aspect can include photoirradiation of the cell with either long UV or NIR light. In further embodiments the method of treating a disease in a subject according to the sixth aspect can include the step of contacting the cell with a prodrug following the photoconjugating step. The prodrug enzyme converts the prodrug to the active form of the drug upon contact of the prodrug with the cell. The affibody portion of the fusion protein can be an anti-epidermal growth factor receptor (EGFR) affibody. In further embodiments the affibody portion of the fusion protein can be an anti-epidermal growth factor receptor (EGFR) affibody with a benzophenone group added at a site-specific mutation to a cysteine residue within the affibody portion. In certain embodiments the method of treating a disease in a subject according to the sixth aspect can the prodrug enzyme can be cytosine deaminase. The disease can be breast cancer. Photoconjugation can be performed using long UV or NIR light in the presence of upconverting nanoparticles.

In a seventh aspect the present invention provides a method of treating cancer. The method can include the steps of contacting a cancer cell with a fusion protein comprising an anti-epidermal growth factor receptor (EGFR) affibody and the prodrug enzyme cytosine deaminase and photoconjugating the fusion protein to the surface of the cell. A benzophenone group can be added at a site-specific mutation within the affibody portion of the fusion protein. In an advantageous embodiment the cancer is breast cancer. The cancer cell can be contacted with a prodrug following the photoconjugating step. The prodrug enzyme can then convert the prodrug to the active form of the drug upon contact of the prodrug with the cell.

In an eighth aspect the present invention provides a method to modify a cell receptor of a target cell with a unique biological tag. The method can include the steps of contacting a cell with a fusion protein comprising an affibody fused to a peptide desired to be presented on a cell surface and photoconjugating the fusion protein to the surface of the cell before or after the fusion protein has been internalized and cycled to the cell surface of a target cell. The affibody portion of the fusion protein can be an anti-epidermal growth factor receptor (EGFR) affibody with a benzophenone group added at a site-specific mutation within the affibody portion.

In a ninth aspect the present invention provides a fusion protein comprising cytosine deaminase (CodA) and an affibody capable of photocrosslinking to epidermal growth factor receptor (EGFR). The EGFR-binding affibody can be conjugated directly to benzophenone (BP) group to facilitate photocrosslinking. Adding a cysteine residue, such as via mutation, can facilitate conjugation.

In a tenth aspect the present invention provides a fusion protein comprising a peptide of interest desired to be expressed on a cell surface and an affibody capable of photocrosslinking to epidermal growth factor receptor (EGFR). The EGFR-binding affibody can be conjugated directly to benzophenone (BP) group to facilitate photocrosslinking. Adding a cysteine residue, such as via mutation, can facilitate conjugation.

In an eleventh aspect the present invention provides a fusion protein comprising a peptide of interest desired to be expressed on a cell surface and an affibody capable of photorosslinking to a cell surface receptor, wherein the affibody is mutated at to have a cysteine residue and the cysteine is conjugated directly to a benzophenone (BP) group.

In a twelfth aspect the present invention provides a method of treating a cell. The method can include the steps of contacting the cell with a fusion protein comprising an affibody fused to an enzyme or an active fragment of an enzyme desired to be presented on a cell surface, photoconjugating the fusion protein to the surface of the cell after the fusion protein has been internalized and cycled to the cell surface of a target cell and contacting the cell with the enzyme substrate. The enzyme portion of the fusion protein can convert the substrate to an active molecule for treating the cell. The photoconjugation can be performed using long UV or NIR light in the presence of upconverting nanoparticles. The prodrug can be administered systemically to a subject having the cell to be treated. In certain embodiments the prodrug is administered about 12 or more hours, about 18 hours or more, or about 24 hours or more after the cell is contacted with the fusion protein.

BRIEF DESCRIPTION OF THE DRAWINGS

For a fuller understanding of the invention, reference should be made to the following detailed description, taken in connection with the accompanying drawings, in which:

FIG. 2 is a set of graphs labeled (A)-(E).

DETAILED DESCRIPTION OF THE PREFERRED EMBODIMENT

The present invention provides a method of affinity-mediated covalent photoconjugation to both confine an enzyme to a cancer cell and, significantly, maintain its expression and activity over multiple days by escaping proteolysis. A number of exquisite reactions have been shown to work both on live cell membranes and in live animals, but these tend to focus on small molecule labels rather than full proteins. Here, it is shown that a covalent bond could mimic the neonatal Fc receptor (FcRn), which is responsible for prolonging the circulation of abundant proteins like albumin and IgG. Because the FcRn binds tightly to the internalized protein, the protein does not desorb from its receptor and is instead recycled out of the cell. Thus, inducing covalent binding of a protein to a target receptor would similarly allow the protein to escape proteolysis and instead be recycled back to the membrane as a permanent fusion to the membrane protein. Thus, rather than losing activity, the enzyme remains presented on the membrane as a functional protein unit over longer time scales, where it can convert multiple prodrug doses into toxic drugs without the need for additional enzyme administrations. Finally, while the work shown here is aimed toward prodrug therapy applications, this method more generally describes a method to modify potentially any specific cell receptor with a unique biological tag without genetic engineering.

Figure 1:
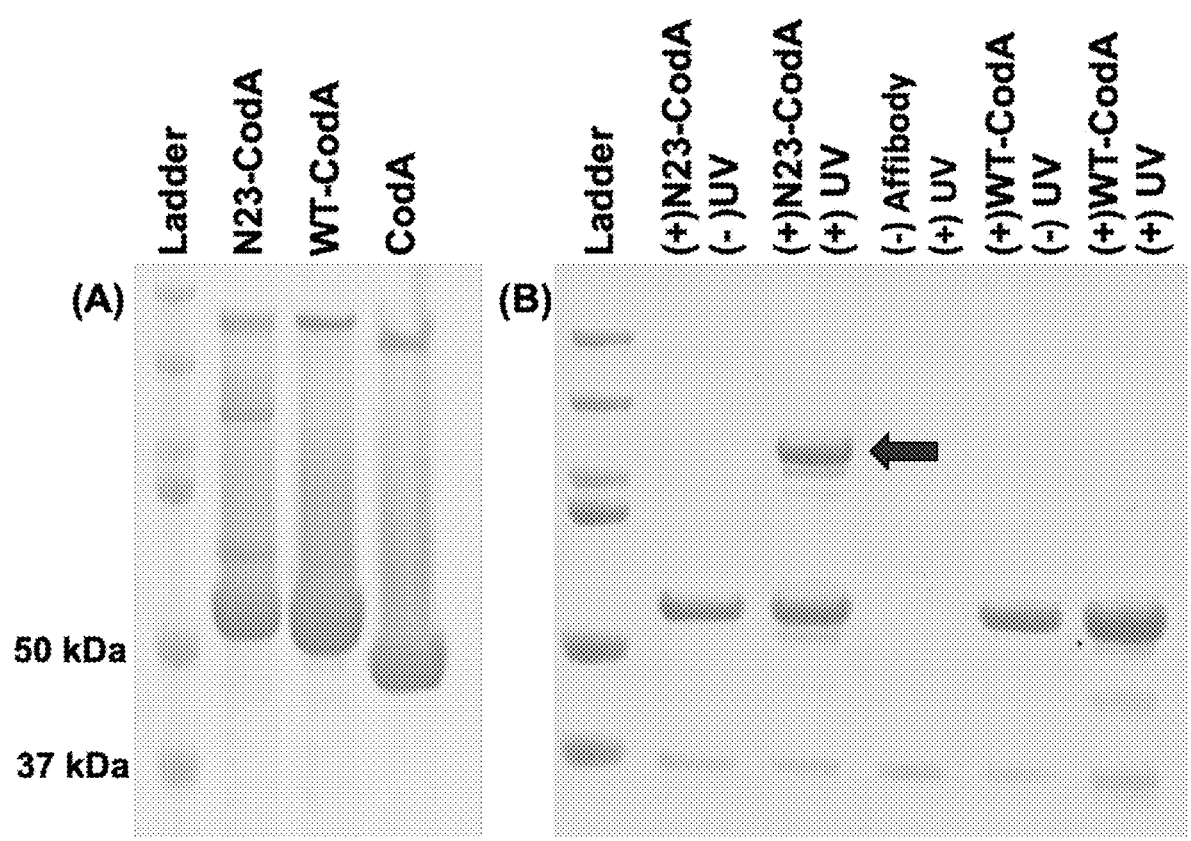
FIG. 1 is a pair of images labeled (A) and (B). (A) SDS-PAGE of purified affibody-enzyme fusion proteins: (left to right) ladder, N23-CodA, WT-CodA, and free CodA. The molecular weights of the ladder proteins are (top to bottom): 200, 150, 100, 75, 50, and 37 kDa. (B) SDS-PAGE of affibody-enzyme fusion proteins photocrosslinked with the soluble extracellular fragment of EGFR. Only the combination of N23-CodA and UV leads to the formation of a new band (arrow). Left to right: Ladder, (+) N23-CodA (+) EGFR (−) UV, (+) N23-CodA (+) EGFR (+) UV, (−) affibody (+) EGFR (+) UV, (+) WT-CodA (+) EGFR (−) UV, and (+) WT-CodA (+) EGFR (+) UV. Ladder molecular weights are same as for (A).
Figure 2A:
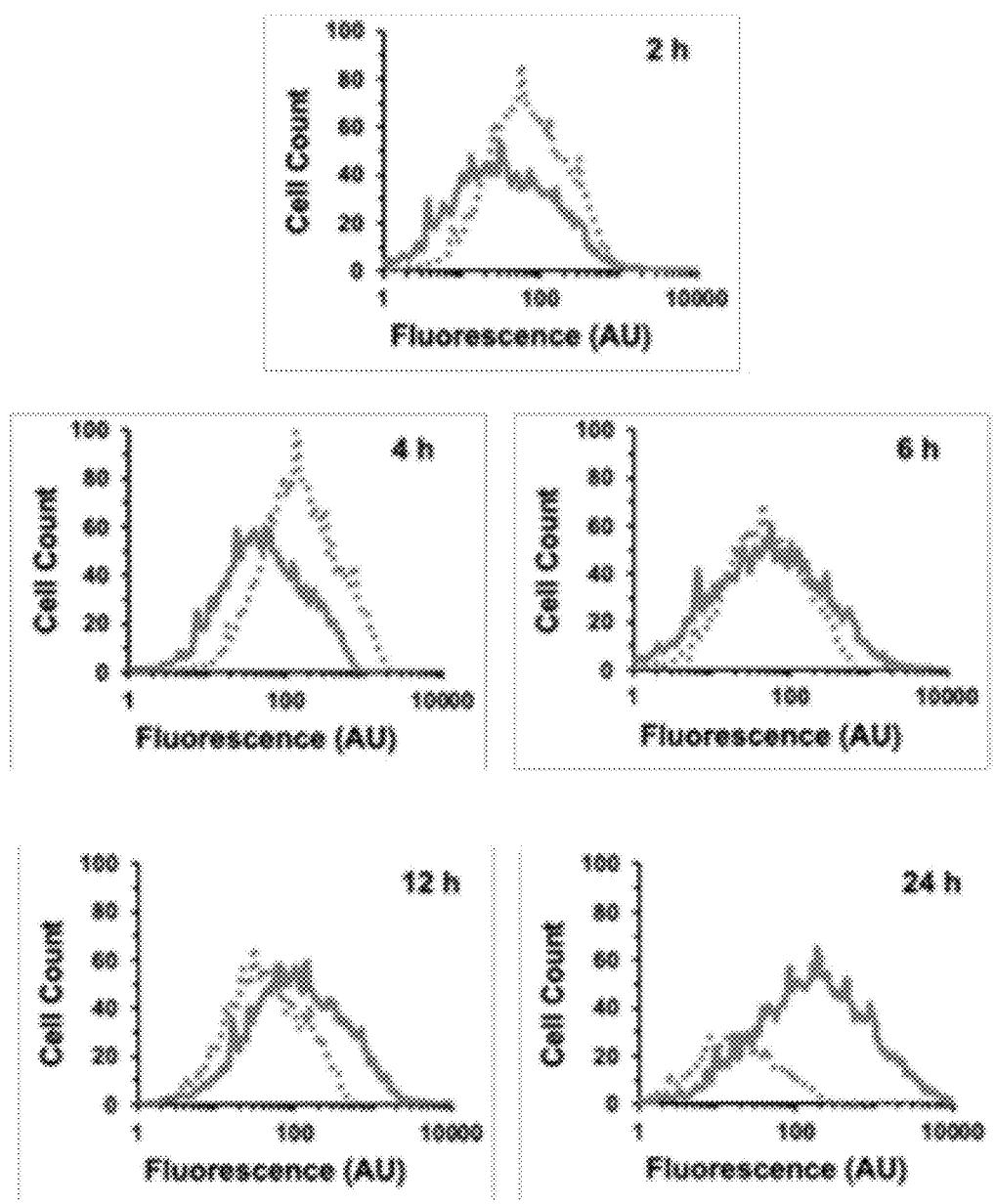
FIG. 2A is a set of representative flow cytometry histograms of MDA-MB-468 cells showing the change in fluorescence intensity of AF488 conjugated to N23-CodA (solid line) and WT-CodA (dotted line) at various times after incubation. Samples were irradiated at the 3 h mark; 2 h samples were not irradiated. Samples were run in triplicate but representative plots are shown for clarity.
Figure 2B:
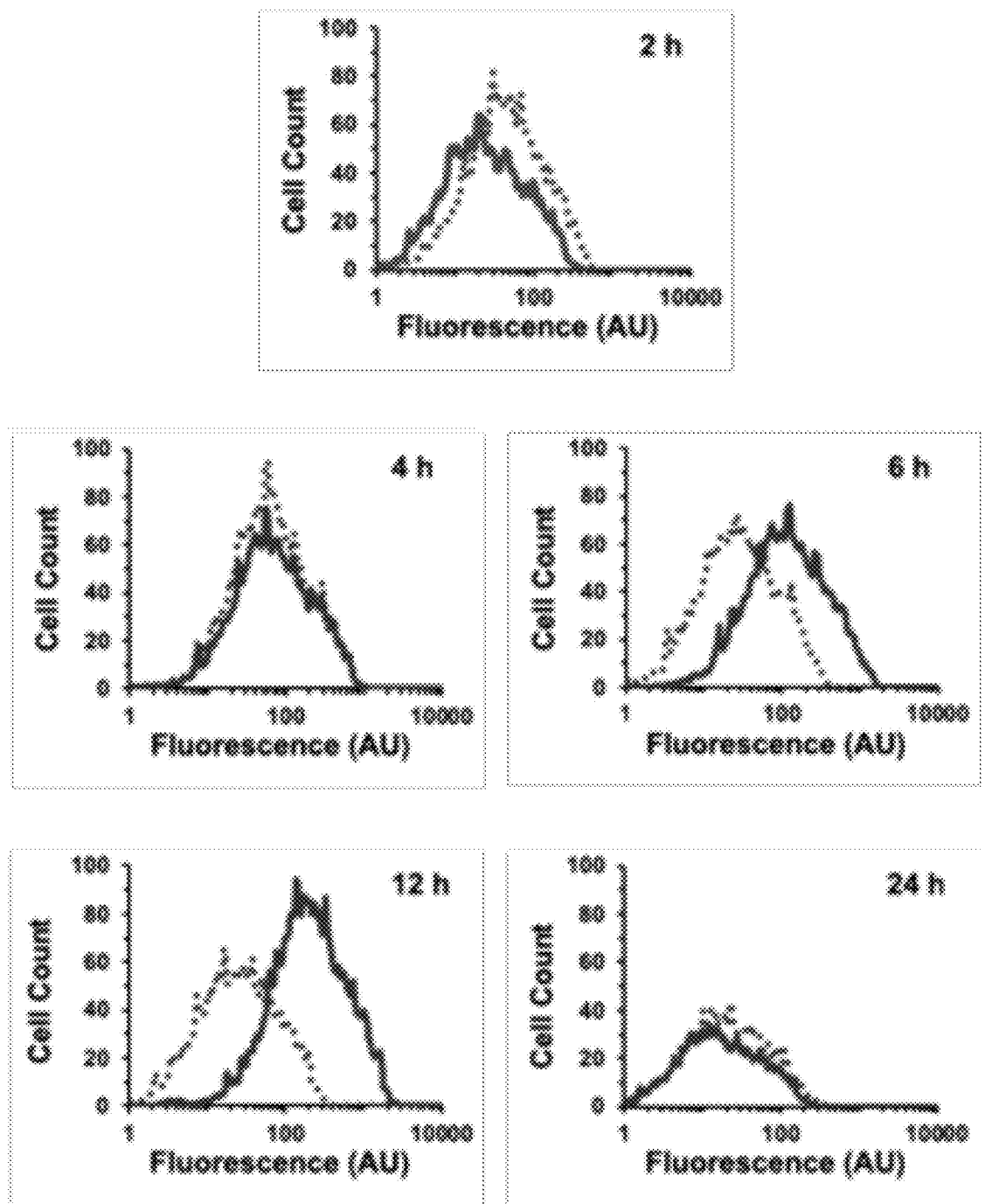
FIG. 2B is a set of representative flow cytometry histograms of MDA-MB-468 cells showing the change in fluorescence intensity of pHAb conjugated to N23-CodA (solid line) and WT-CodA (dotted line) at various times after incubation. Samples were irradiated at the 3 h mark; 2 h samples were not irradiated. Samples were run in triplicate but representative plots are shown for clarity.
Figure 2C:
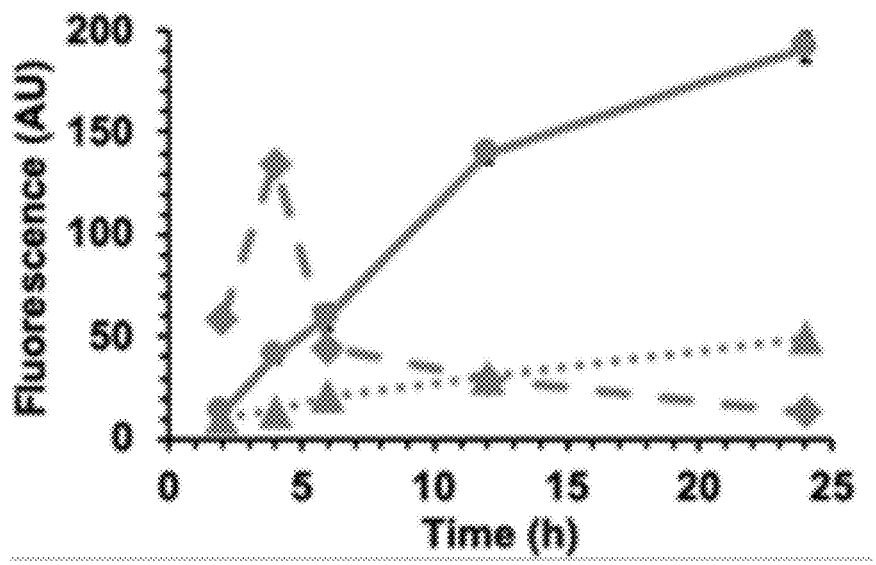
FIG. 2C is a graph showing the change of mean fluorescence intensity with time of AF488 conjugated to N23-CodA (solid line) and WT-CodA (dashed line). Dotted line shows fluorescence from N23-CodA with EGF added.
Figure 2D:
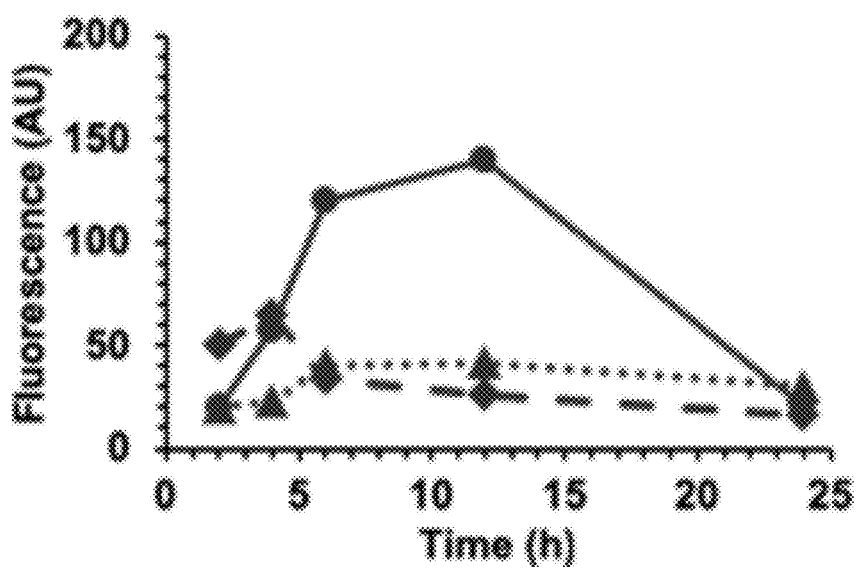
FIG. 2D is a graph showing the change of mean fluorescence intensity with time of pHAb conjugated to N23-CodA (solid line) and WT-CodA (dashed line). Dotted line shows fluorescence from N23-CodA with EGF added.
Figure 2E:
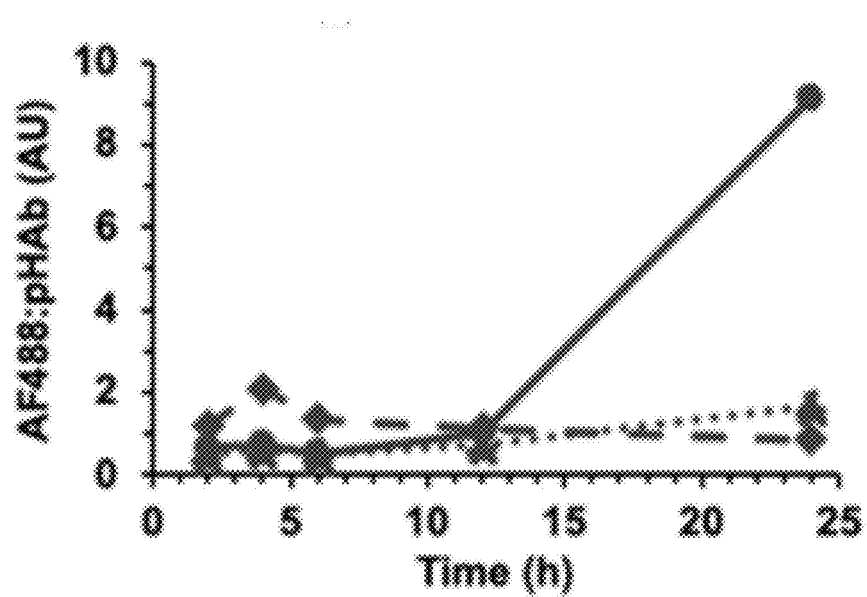
FIG. 2E is a graph showing the ratio of AF488:pHAb fluorescence for N23-CodA (solid), WT-CodA (dashed), and N23-CodA+EGF (dotted) as function of time. For C-E, error bars represent standard error; in some cases the error range is smaller than the data marker.

In order to show retention of prodrug enzyme activity after photoconjugation to a cell receptor, a fusion protein was created consisting of cytosine deaminase (CodA) and an affibody capable of photocrosslinking to epidermal growth factor receptor (EGFR), its target ligand. EGFR-binding affibody $Z_{EGFR:1907}$ (henceforth known as wildtype, or WT), once mutated specifically at its N23 position to a cysteine could then be conjugated directly with benzophenone (BP). Upon photoirradiation with either long UV or NIR light in the presence of upconverting nanoparticles, the BP modified affibodies (N23BP) became covalently conjugated to either pure EGFR or EGFR expressed on cells in both 2- and 3D models. N23BP EGFR binding affibodies were fused with cystosine deaminase (CodA), a bacterial enzyme encoded by the CodA sequence of E. coli that can convert 5-fluorocytosine (5-FC) prodrug to toxic 5-fluorouracil (5-FU) and thus has been used frequently in ADEPT. As with the affibodies alone, the fusion proteins were expressed in the E. coli strain BL21(DE3) and purified from cell lysate by Ni-NTA bead capture. The purified proteins were then reacted with maleimide-benzophenone (BP), followed by removal of excess BP through 20 kDa MWCO dialysis cups (Thermo Fisher). Using similar protocols, proteins were expressed consisting of WT affibody-fused CodA (WT-CodA), as well as CodA alone without affibody. Each of these proteins possessed expected molecular weights when analyzed by SDS-PAGE (FIG. 1).

Figure 18:
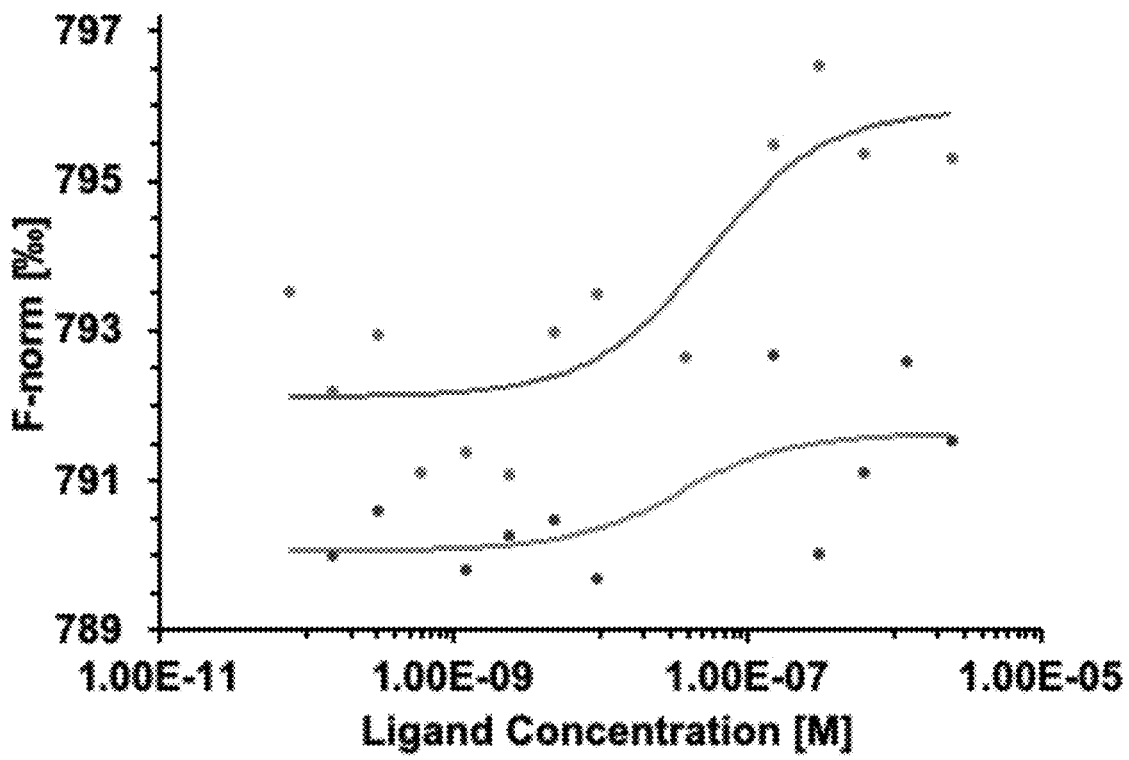
FIG. 18 is a graph depicting a comparison of microscale thermophoresis (MST) signal vs. affibody concentration for both N23BP-CodA (upper line) and WT-CodA (lower line) affibody-enzymes against 10 nM of extracellular purified human EGFR, labeled with Alexa Fluor 647.
Figure 19:
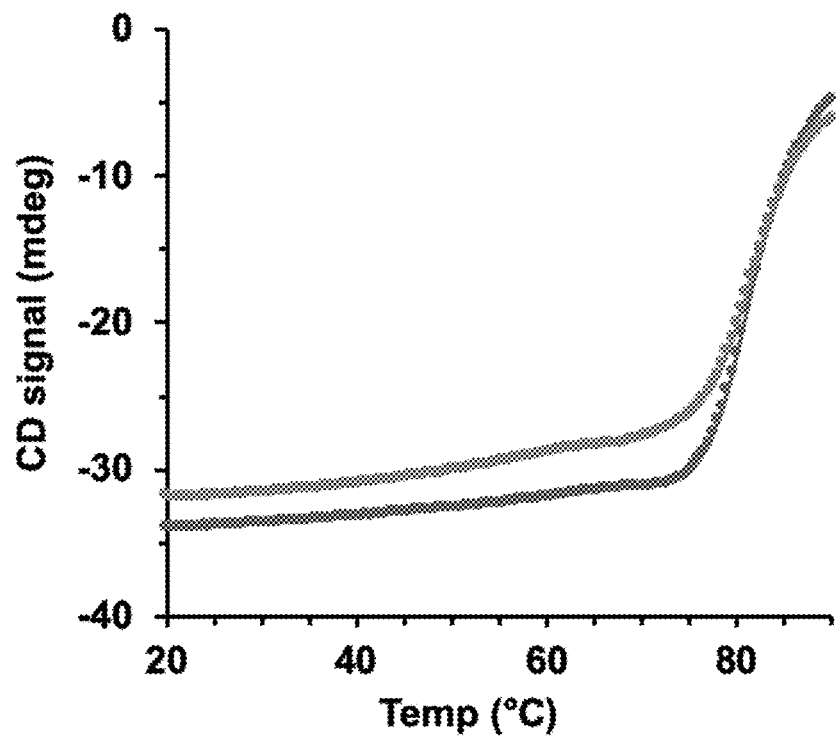
FIG. 19 is a graph depicting melting curves showing circular dichroism at 222 nm vs. temperature for both N23BP-CodA (lower line/plot) and WT-CodA (upper line/plot) affibody-enzyme fusion proteins.

The affibody-enzyme fusions were next characterized to ensure that they possessed EGFR-binding and photocrosslinking similar to free affibodies. First, non-covalent affinity for EGFR was tested by microscale thermophoresis measurements (MST). For this, the purified soluble fragment of EGFR was conjugated to Alexa Fluor 647 (Thermo Fisher) and mixed with various concentrations of affibody-enzyme fusion proteins ranging from 10 µM to 100 µM. From these measurements, KD values were obtained showing KD=25 nM±0.66 nm and 44 nM±1.02 nm for WT-CodA and N23-CodA, respectively (FIG. 18). While these values are approximately an order of magnitude higher than that of the reported free affibody (KD~ 2.8 nM), they are still well within nanomolar range. Interestingly, the N23-CodA fusion proteins displayed more favorable binding to EGFR than BP-substituted N23 affibody alone, which may be attributed to reduced solubility of the small affibodies after conjugation with benzophenone and dyes. Finally, temperature-dependent circular dichroism studies showed that the melting temperature of both affibody-enzyme fusion proteins (~80° C.) were similar to the reported value for free CodA (85° C.±2° C.), which shows that the enzyme structure is not likely to be compromised as a result of affibody fusion (FIG. 19).

Next, the affibody-CodA fusion proteins were tested for photocrosslinking to pure EGFR. First, wild-type affibody-enzyme (WT-CodA), BP-modified mutant affibody-enzyme (N23-CodA), and the enzyme itself (CodA) were each mixed with purified soluble fragment of EGFR and irradiated with 890 µW/cm$^2$ of 365 nm light for 30 min, which is within recommended limits and does not harm biological samples. Following deglycosylation and thermal denaturation (see Methods), each mixture was run on a SDS-PAGE gel. While the WT-CodA reaction with EGFR yielded only individual bands corresponding to either the affibody-enzyme alone (57 kDa) or the soluble purified EGFR fragment (40 kDa), the BP-containing N23-CodA fusion protein showed successful photocrosslinking to EGFR after irradiation as observed by the appearance of a new band >100 kDa, which is the sum of the molecular weights of EGFR and N23-CodA. Thus, these results show that despite the affibody being fused to cytosine deaminase, the BP containing affibody was successfully photocrosslinked to EGFR (FIG. 1).

Figure 20:
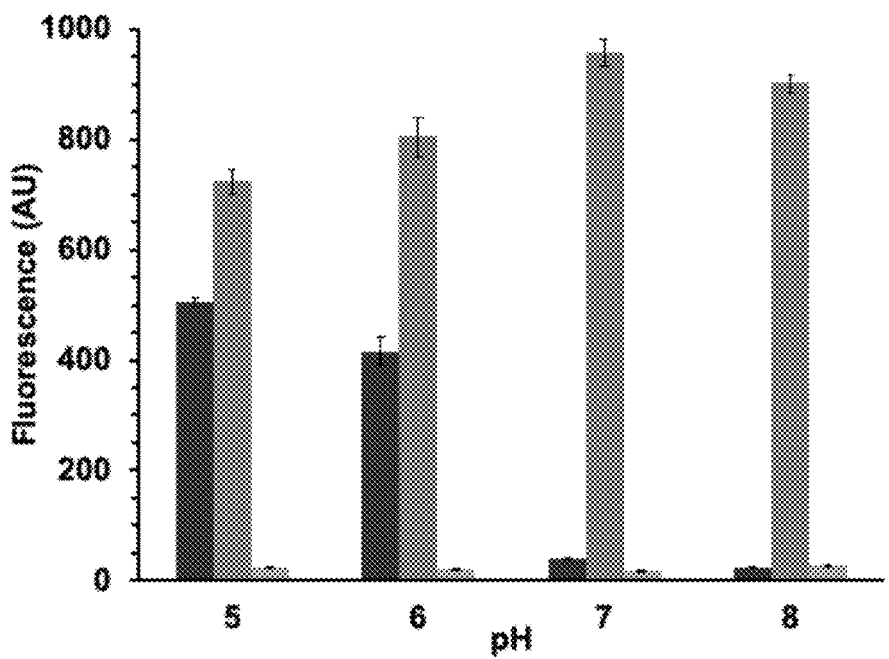
FIG. 20 is a graph depicting a comparison of fluorescence of pHAb (pH-dependent, left) and AF488 (pH independent, center) dyes at different pH; blank PBS (right) is shown for comparison. Error bars represent standard error from three measurements.
Figure 21:
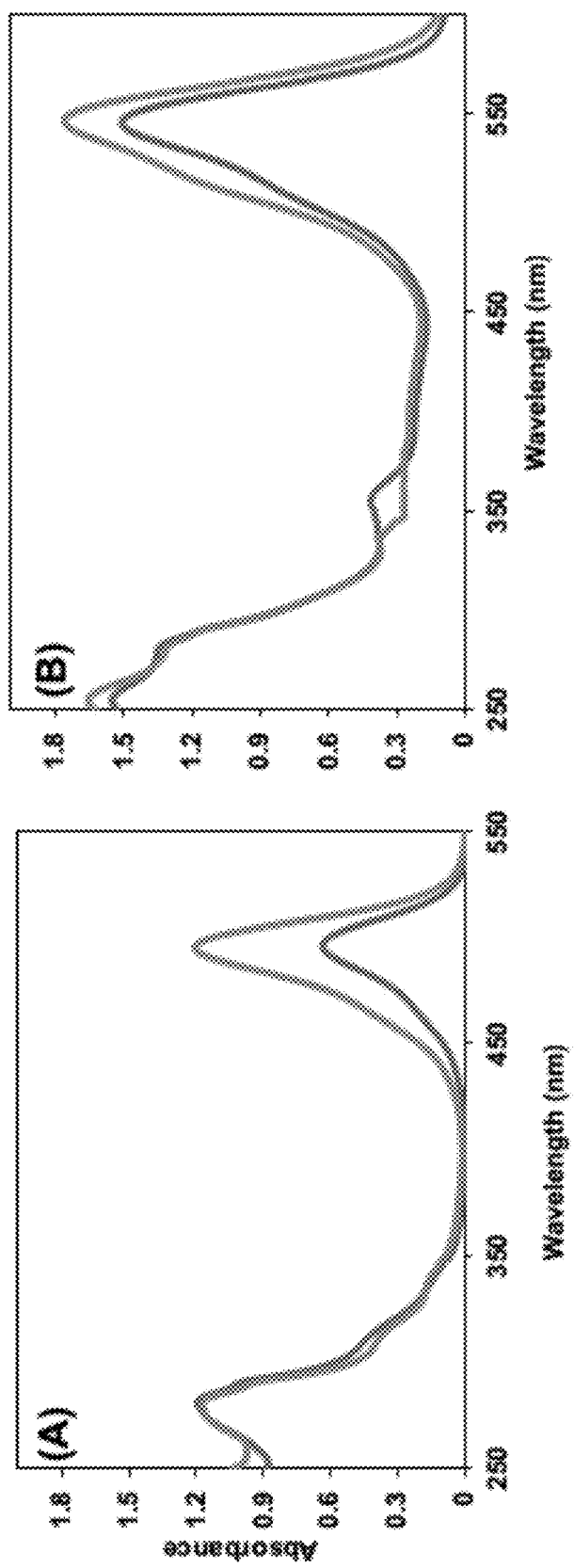
FIG. 21 is a pair of graphs depicting the change of mean fluorescent intensity with time of (A) AF488 and (B) conjugated to WT-CodA (dashed line) and WT-CodA with free EGF added (dotted line).

The next step was to track the fate of the fusion proteins once bound or crosslinked to receptors on live cells. Anticipating receptor-mediated endocytosis, two dyes were conjugated to the fusion proteins: pH-tolerant, green-fluorescent AlexaFluor 488 (AF488, Thermo Fisher), and the pH-sensitive dye pHAb (Promega), which shows strong emission in the red (580 nm) at pH<6.5 (endosome), but has low photoluminescence at pH>6.5 (cytosol/external fluid) (FIG. 20). To attach the dyes, the affibody-enzyme fusion proteins were first reacted with either NHS-AF488 or NHS-pHAb at 10:1 molar ratios of dye:protein for 2 hr at room temperature, followed by dialysis to remove any unreacted fluorophore. On average, this approach yielded a degree of labeling of ~-1.2 moles of dye per mole protein as determined from UV-Vis spectra (FIG. 21). Next, each form of affibody-CodA (WT, N23BP) was incubated with EGFR-positive MDA-MB-468 human breast carcinoma cells (~30,000 cells/well). After 3 hr of incubation, the cells were irradiated with 890 µW/cm$^2$ of 365 nm light for 30 min. Finally, cells were harvested at 2, 4, 6, 12, or 24 h (cells incubated for only 2 hr were not irradiated) by washing three times to remove excess affibody-enzyme, trypsinized, and fixed with 4% paraformaldehyde. The cells were then transferred to PBS and the cell suspension was analyzed in a BDFACSCelesta flow cytometer (BD Biosciences) with simultaneous 488 laser and 561 laser excitation for tracking AF488 and pHAb, respectively.

Figure 22:
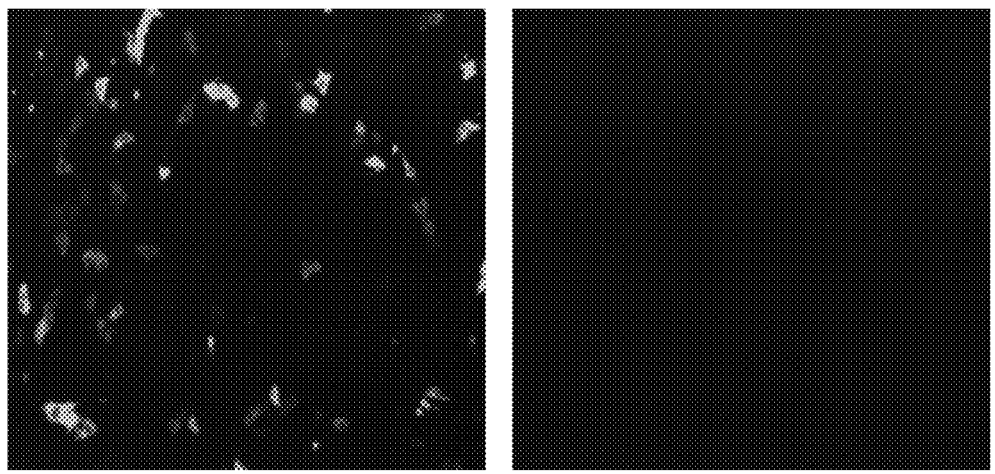
FIG. 22 is a pair of images showing fluorescence microscopy images comparing (left) EKAR-transfected and (right) non-transfected cells. The green fluorescence (left image—light gray in gray scale) from the cells from the EKAR indicates successful transfection.

While cells incubated with WT-CodA showed only a short increase in AF488 fluorescence at 2 h followed by a steady decrease (FIG. 2), the cells that were treated with N23-CodA demonstrated a marked, progressive increase in fluorescence per cell over a time period as long as 24 hours. These results are consistent with results showing that N23 affibodies were retained in 2- and 3D tumor models, while WT affibodies showed a significant decrease in EGFR binding after 4 hours. The pHAb fluorescence of the WT-CodA proteins followed a similar trend, peaking at 2 hr and decreasing thereafter. In direct contrast, however, the pHAb fluorescence of the N23-CodA shows that the photoconjugated N23-CodA proteins are first taken into endosomes—reaching a maximum fluorescence at 12 hr incubation—followed by a decline at 24 hours. To confirm both the specificity of EGFR targeting and that fusion protein uptake is an EGFR-mediated process, the above experiment was repeated with addition of equimolar free Epidermal Growth Factor (EGF), which led to reduced retention of N23-CodA in cells. This effect, which is attributed to competition of EGF and affibody-enzyme for EGFR binding sites, was also observed for the accumulation of dye conjugated WT-CodA affibody-enzymes (FIG. 22).

Figure 3:
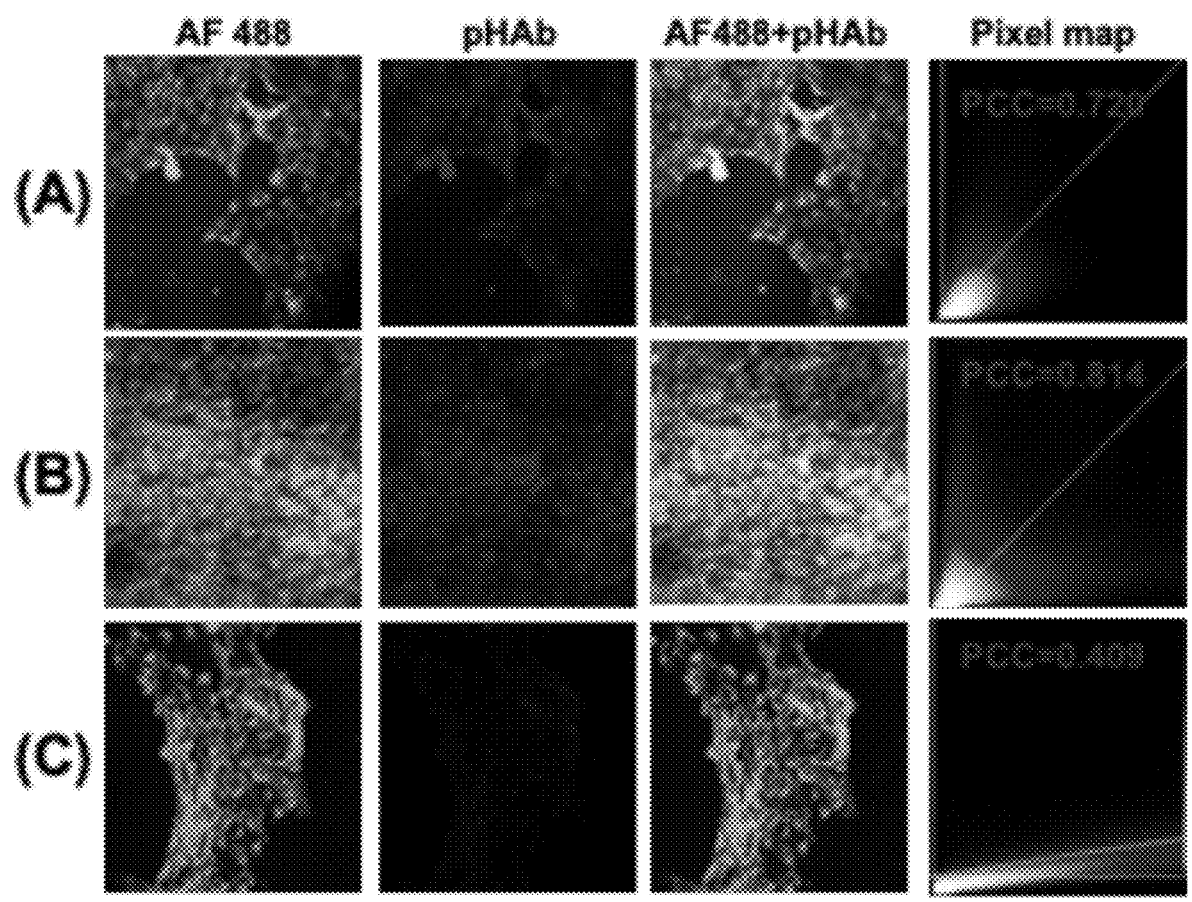
FIG. 3 is a set of images labeled (A)-(F). (A-C) Confocal microscopy images of MDA-MB-468 breast cancer cells treated with AF488-pHAb-N23-CodA for (A) 4 h, (B) 12 h, and (C) 24 h. The pixel map shows the colocalization of the two dyes (x: green, y: red) with the reported Pearson Correlation Coefficient (PCC). (D-F) Confocal microscopy images of MDA-MB-468 breast cancer cells treated with AF488-pHAb-WT-CodA for (D) 4 h, (E) 12 h, and (F) 24 h, with pixel map showing colocalization and PCC.

In addition to flow cytometry, confocal microscopy was utilized to examine the fate of affibody-enzymes in MDA-MB-468 cells. The cells were grown on poly D-lysine coated glass coverslips (Corning BioCoat) and incubated with either AF488-pHAb-N23-CodA or AF488-pHAb-WT-CodA. After 3 hr, the cells were irradiated for 30 min as described above. At 4, 12 and 24 hr total incubation, the cells were washed and incubated with the nuclear stain 4',6-diamidino-2-phenylindole (DAPI) for 10 min. The cells were washed again three times with PBS before mounting the cells with Prolong Gold antifade mountant (Thermo Fisher) and then imaging with a Nikon AiR Laser Confocal Microscope. For cells with WT-CodA, significant fluorescence was observed in both the green and red channels at 4 hr, corresponding to AF488 and pHAb, respectively (FIG. 3). However, both channels showed marked decrease in fluorescence at 12 and 24 hours. For the cells with N23-CodA, bright fluorescence was observed in both the green and red channels at 4 hr and 12 hours. At 24 hr, however, a strong green fluorescence was observed with a dim red fluorescence, which is consistent with the theory that the photocrosslinked affibody-enzyme is being recycled back to the cell membrane. To quantify the relationship between AF488 and pHAb fluorescence, colocalization analysis was performed on the images from the green and red channels without thresholding. A heat map of normalized pixel intensities is shown in FIG. 3, along with a Pearson Correlation Coefficient to provide a measure of colocalization. For the WT-CodA, a PCC of 0.601 was found at 4 hr, which is consistent with considerable pixel overlap. At 12 and 24 h, however, the PCC decreases to 0.494 and 0.313, with likely capture of green AF488 emission in the red channel. For N23-CodA, high PCC values of 0.720 and 0.814 were obtained at 4 h and 12 h. At 24 h, when green fluorescence is mostly present, the PCC drops to 0.409. Thus, the N23-CodA appears to retain its structure at 12 h when non-covalently bound proteins would otherwise be degraded, while the red fluorescence drops away at 24 h as was observed in the flow cytometry studies, indicating that the N23-CodA leaves the endosome intact.

Figure 4:
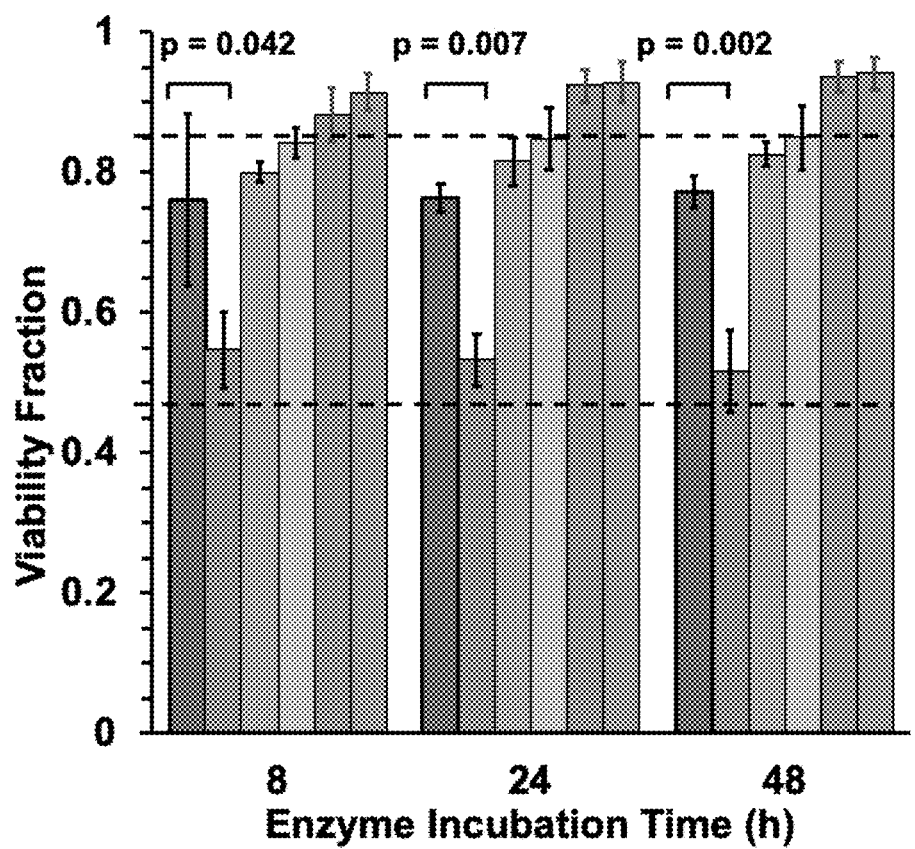
FIG. 4 is a graph depicting cell viability fraction of MDA-MB-468 cells in combination with affibody-enzyme fusion proteins, 5-fluorocytosine pro-drug, and UV light, as measured by MTT assay. Top dotted line: baseline viability of cells incubated with 5-FC prodrug (0.854). Middle dotted line: baseline viability of cells incubated with 5-FU drug (0.467). Left to right at each timepoint: (+)WT-CodA (+)5-FC (+)UV, (+)N23-CodA (+)5-FC (+)UV, (+)CodA (+)5-FC (+)UV, (+)N23-CodA (+)5-FC (−)UV, (+)N23-CodA (−)5-FC (+)UV, and (+)N23-CodA (−)5-FC (−)UV. Error bars represent standard error.
Figure 5:
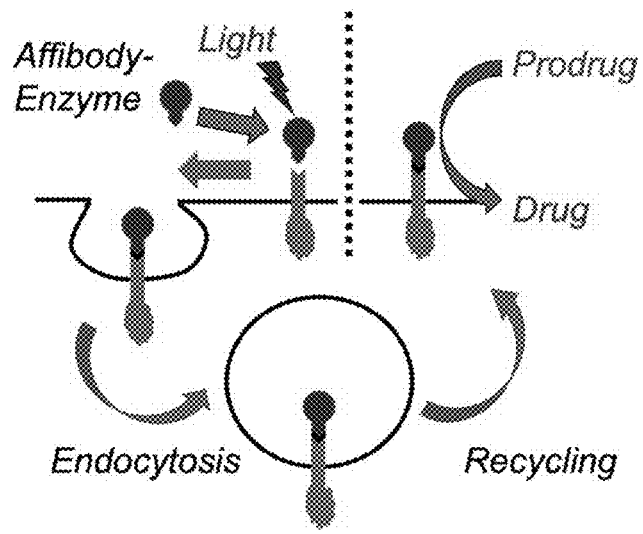
FIG. 5 is a drawing depicting that enzymes photocrosslinked to live cell receptors retain activity after both internalization and recycling.
Figure 6:
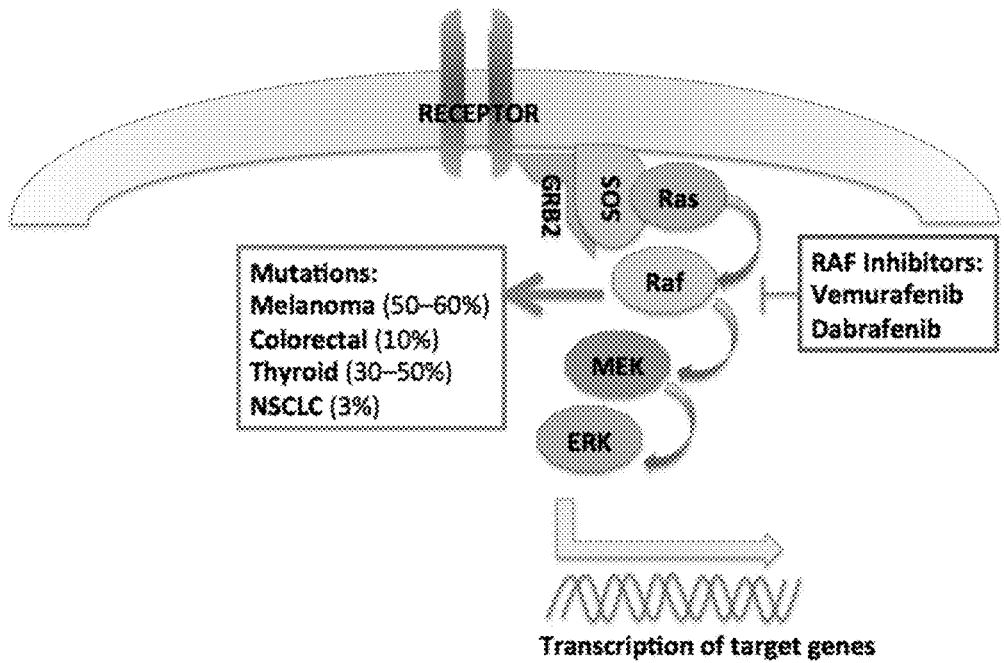
FIG. 6 is a drawing depicting clinically approved targeted therapies.
Figure 7:
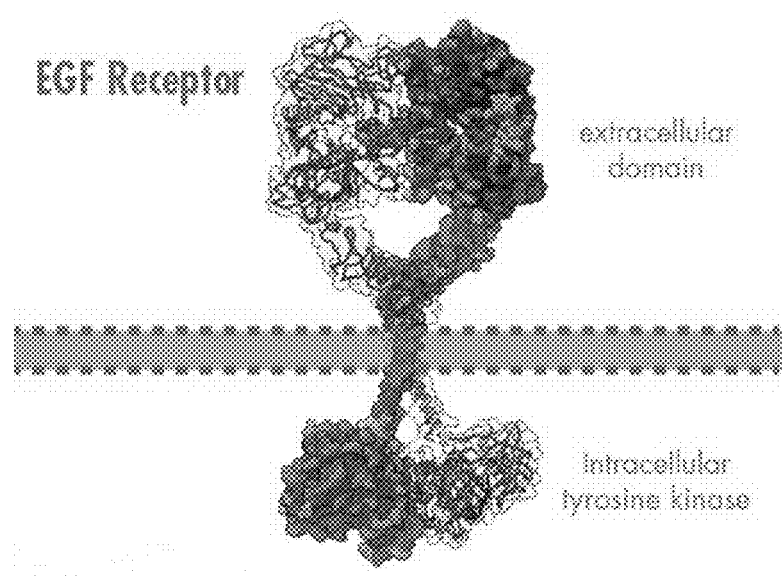
FIG. 7 is a drawing depicting Epidermal Growth Factor Receptor (EGFR) as a target. EGFR is a trans-membrane protein. Upon binding to EGF, auto-phosphorylation occurs. Many tumors overexpress EGFR; show abnormal cell division.
Figure 8:
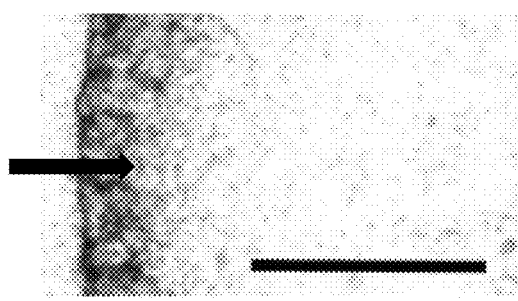
FIG. 8 is an image depicting challenges with targeted therapy. mAb's show poor diffusion. TKI's show rapid clearance.
Figure 9:
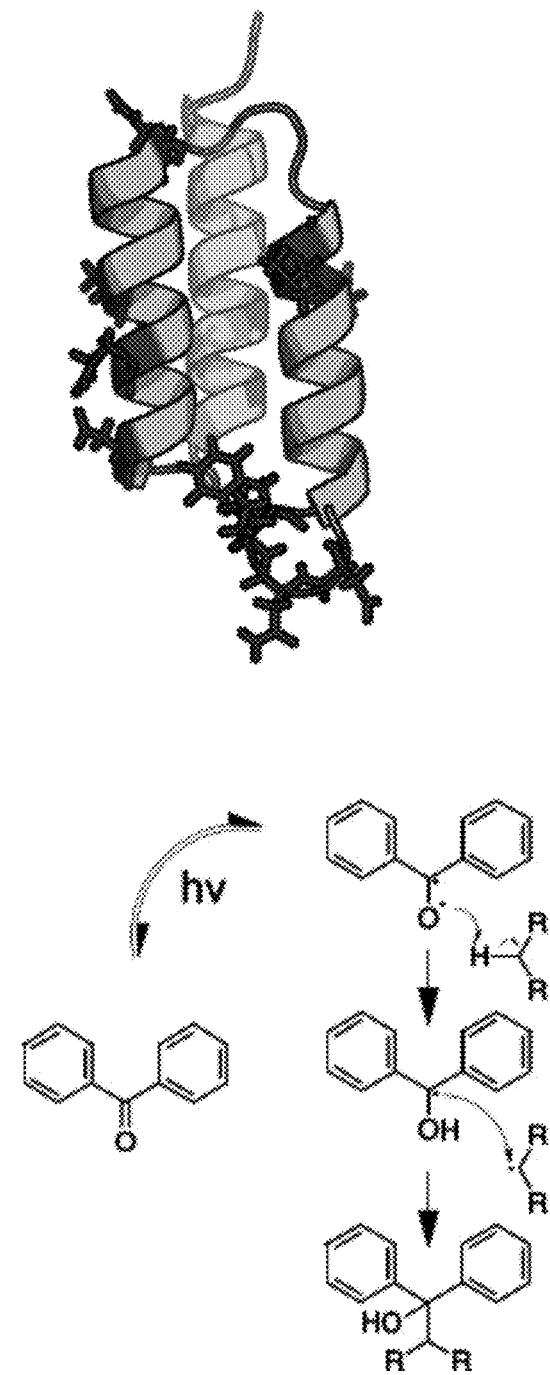
FIG. 9 is a pair of drawings depicting affibodies as alternatives to conventional therapy. Triple alpha helix of the affibody with 58 amino acids. A randomization of thirteen amino acids imparts unique binding properties. A cysteine mutation to conjugate a photo-crosslinker.
Figure 10:
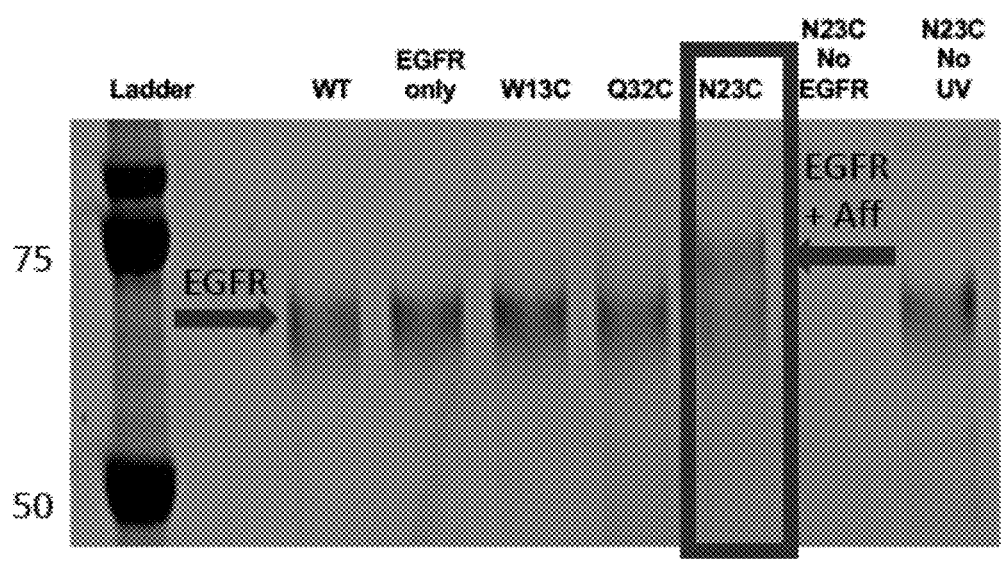
FIG. 10 is an image depicting an affibody mutation to facilitate crosslinking. Affibodies were expressed in $E.\ coli$ and purified by Ni-Agarose gels. Only N23C showed successful crosslinking. 2 affibodies: (1) WT (binds but doesn't crosslink to EGFR); (2) N23C (binds and crosslinks).
Figure 11:
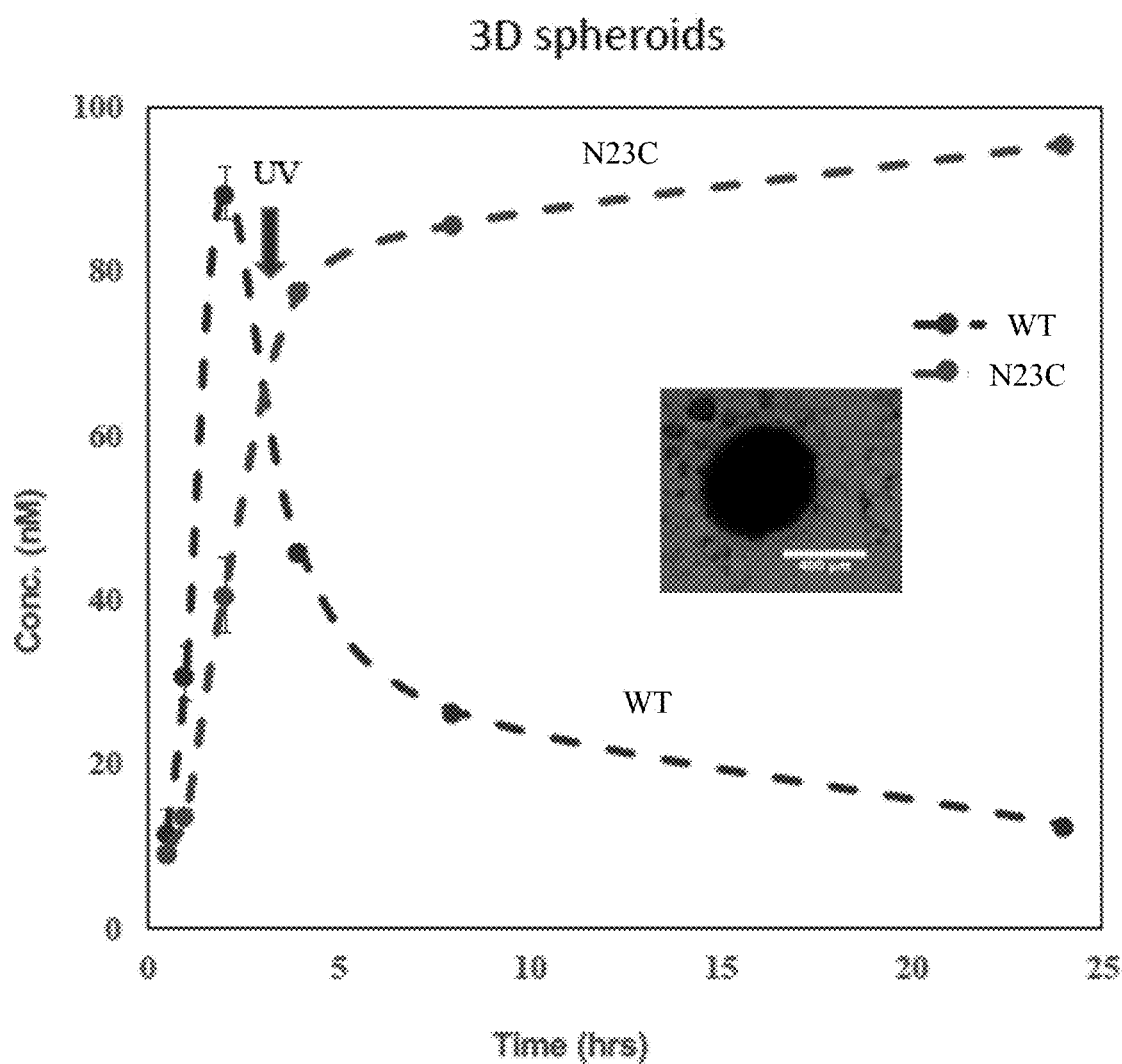
FIG. 11 is a graph depicting retention of affibodies in EGFR (+) cancer cells. N23C is the upper plot in the 5 to 25 hour timepoints.
Figure 12:
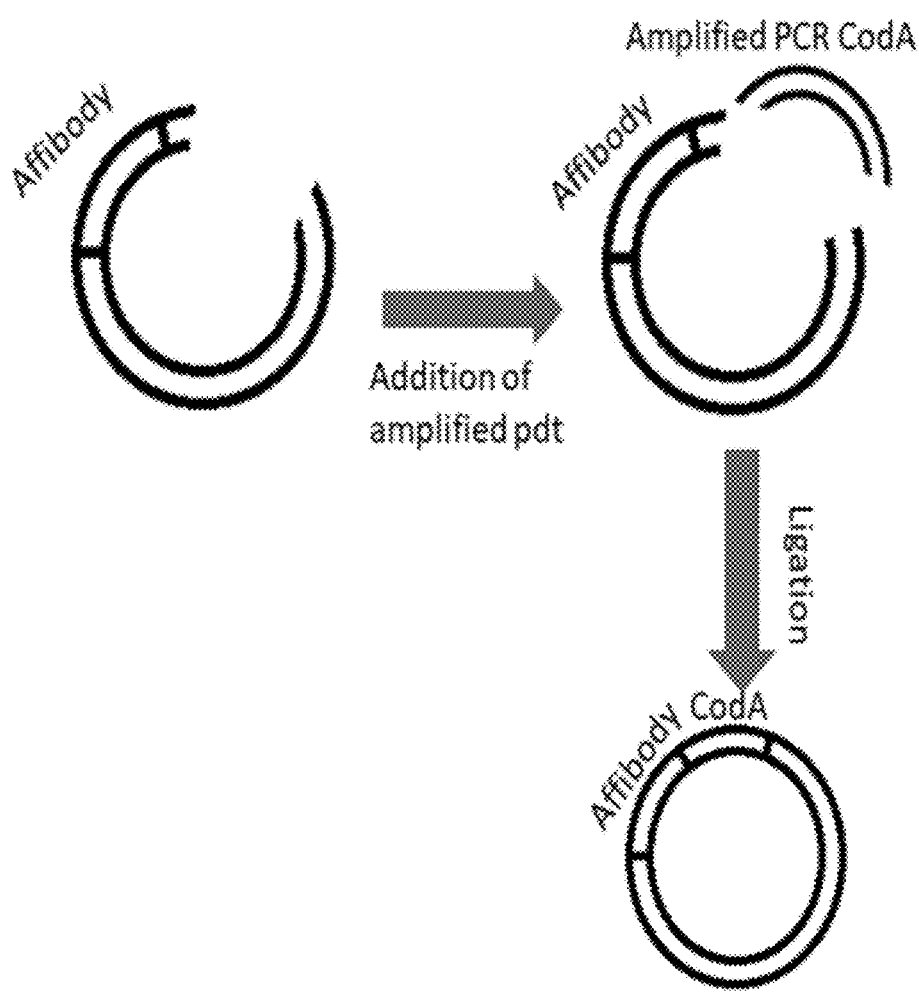
FIG. 12 is a diagram. Affibodies used for EGFR (+) cancer cell apoptosis. Cytosine Deaminase encoded by CoDA gene in $E.\ coli$. CodA gene ligated to the affibody construct. The affibody-enzyme construct converts 5FC (prodrug) to 5FU (drug). (1) Study the therapeutic effects. (2) Investigate the retention mechanism.
Figure 13:
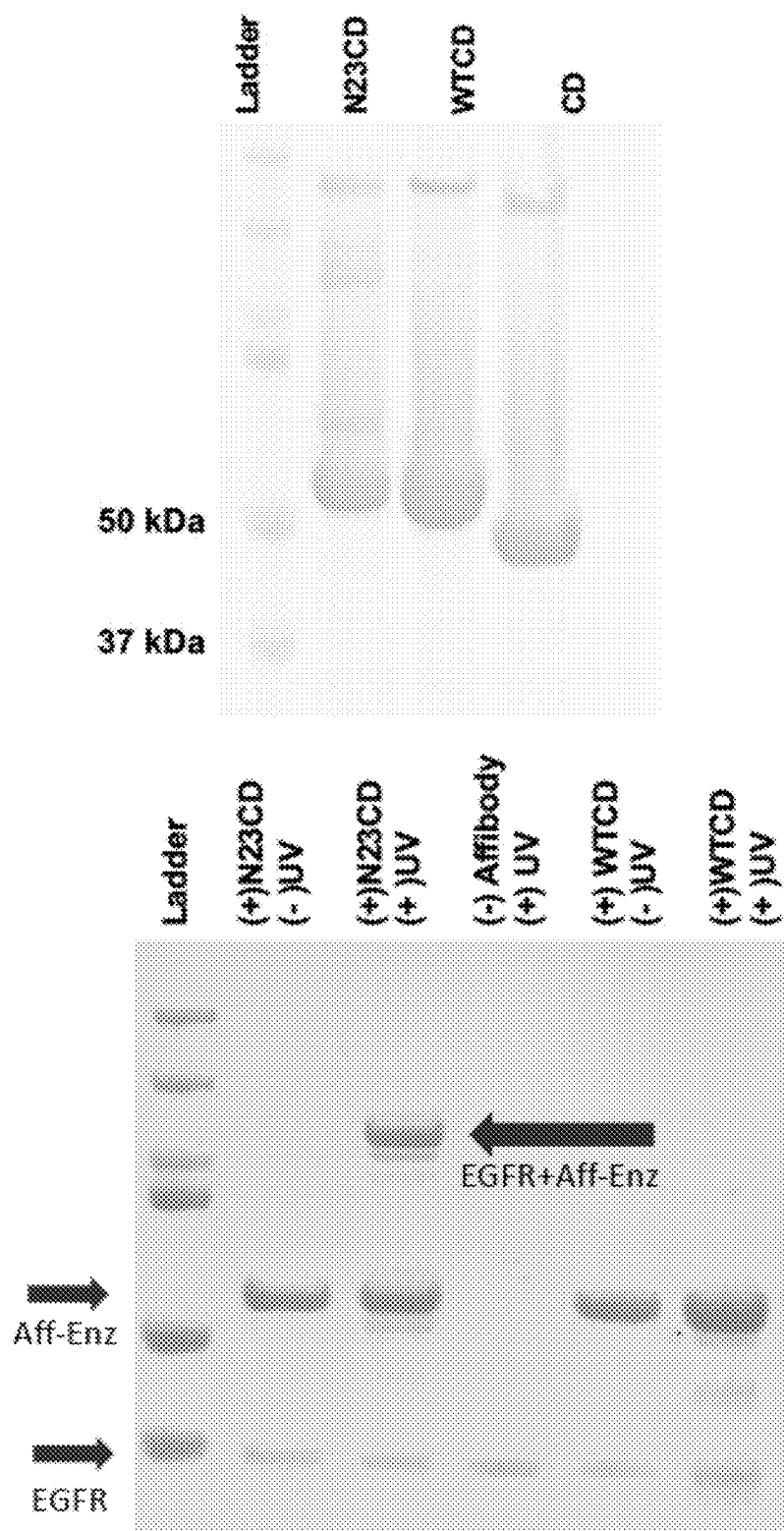
FIG. 13 is an image of SDS-PAGE gels of fusion affibodies. See also FIG. 1.
Figure 14:
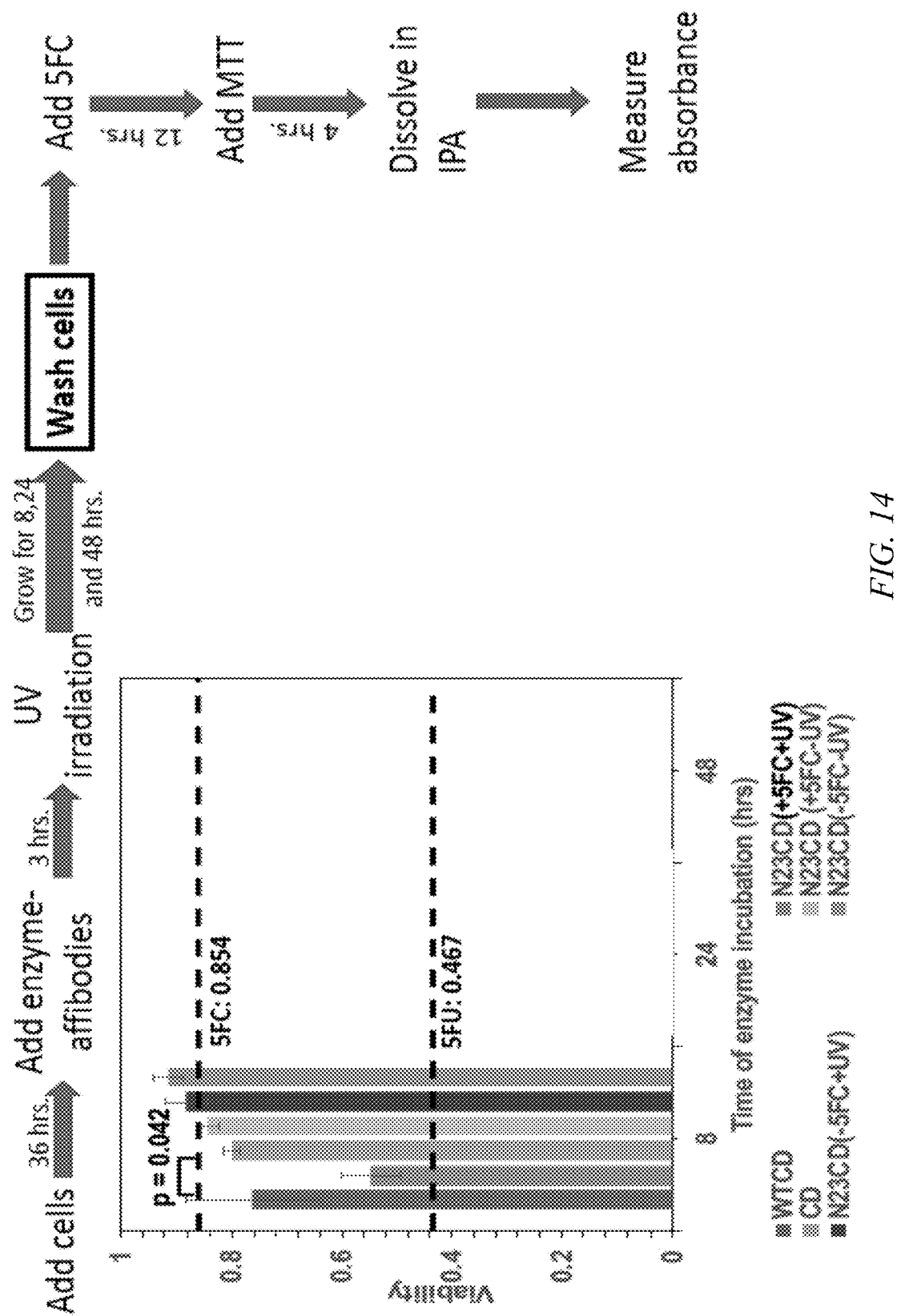
FIG. 14 is a graph and a diagram depicting an MTT Assay with MDA MB 468 cells.
Figure 15:
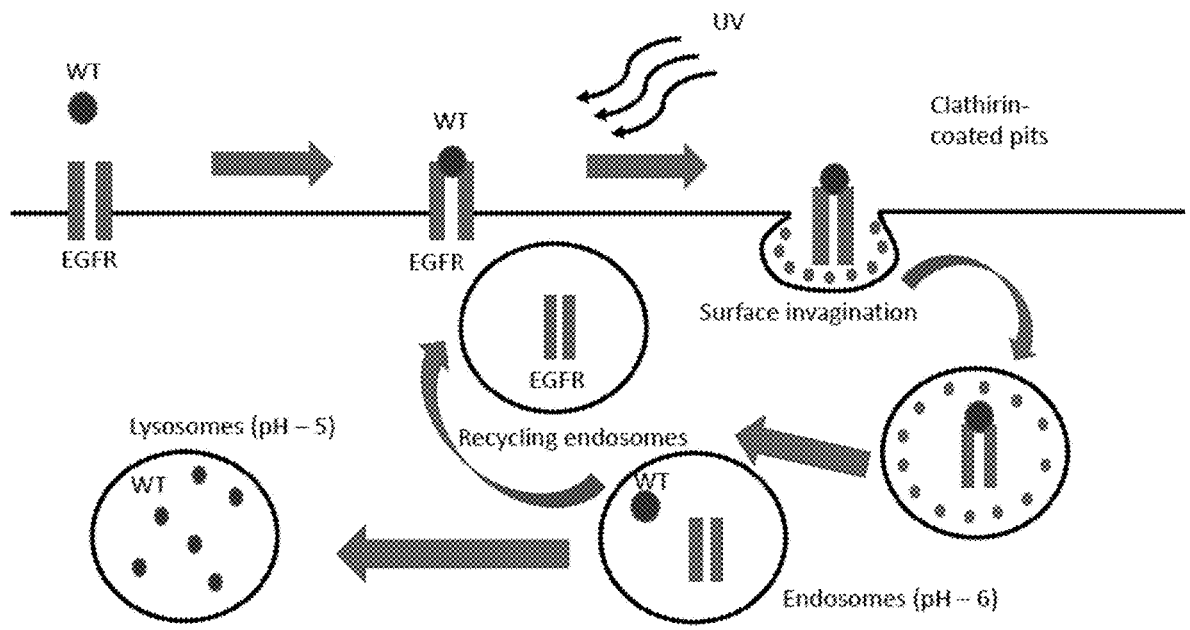
FIG. 15 is a diagram depicting the endocytic pathway for WT.
Figure 16:
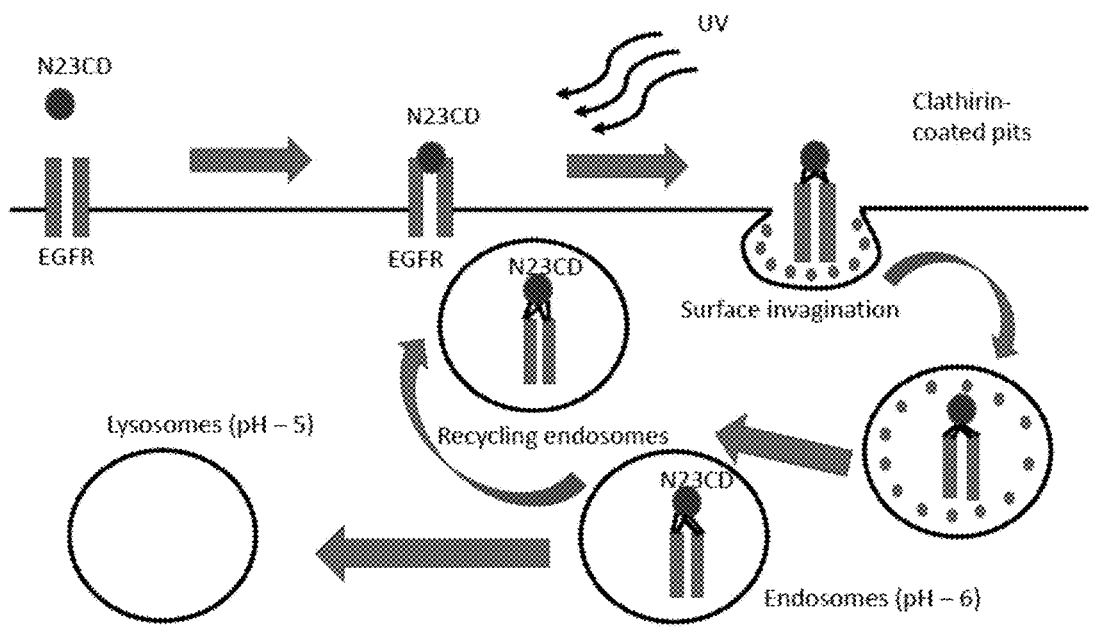
FIG. 16 is a diagram depicting the endocytic pathway for N23CD.
Figure 17:
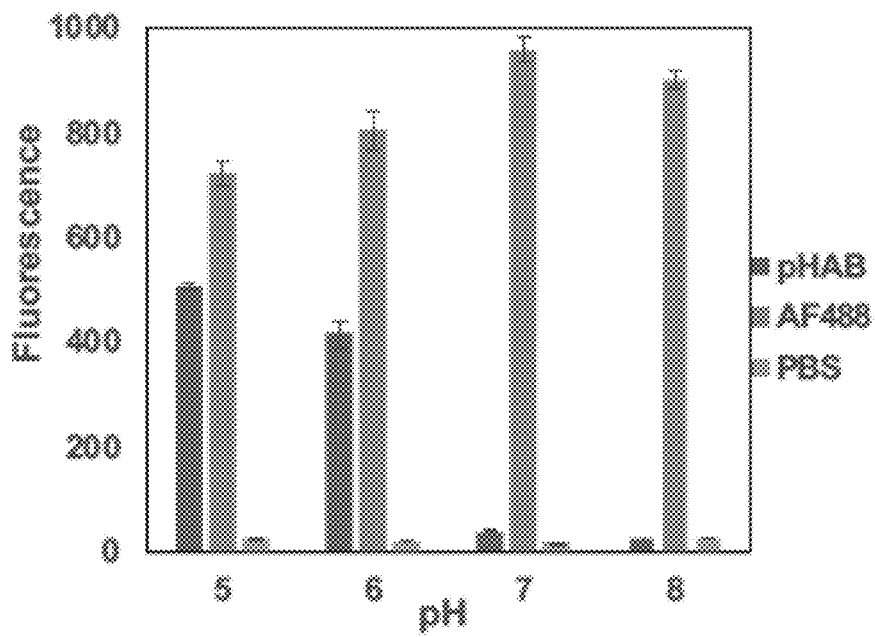
FIG. 17 is a graph depicting testing the hypothesis with flow cytometry.

Finally, having established both the photocrosslinking of the N2-CodA affibody-enzyme to EGFR on living cells and retention of protein expression before and after endocytosis, the enzymatic activity of the fusion proteins was then leveraged for cell killing by prodrug conversion. First, as determined by measuring cytosine conversion to uracil by UV-Vis spectroscopy, the KM and kcat of the affibody-enzyme fusion proteins (N23 and WT) were within 70% of those displayed by the native enzyme (FIG. 22, Table 1). Next, prodrug therapy experiments were run against MDA-MB-468 cells in vitro. In 96-well plates, cells were incubated with 1 μM of WT-CodA, N23-CodA, or CodA alone. As before, after 3 h the cells were irradiated with 365 nm light for 30 min followed by further incubation to a total time of 8, 24, or 48 h. When each time point was reached, the excess affibody-enzymes were removed by washing the cells three times with PBS, and 2 mM of 5-FC was added. Three control samples were also included: 1) (+)UV, (−)5-FC, 2) (−)UV, (+)5-FC, and 3) (−)UV, (−)5-FC. A few wells also contained just 5-FC (prodrug) and 5-FU (drug) to establish baseline toxicities. After 12 h incubation with 5-FC, excess pro-drug was removed, cells were washed with PBS, and viability was measured by MTT assay. Cells treated with WT-CodA or free CodA showed ~70-80%±1-4% viability (FIG. 4), slightly less than the 5-FC baseline viability of 85%±2%. However, photocrosslinked N23-CodA proteins incubated with 5-FC showed a marked decrease in viability to ~50-55%±2.5%, similar to the baseline 5-FU toxicity (47%±2.6%). The differences in cell viability between N23-CodA and WT-CodA were found to be statistically significant, with p<0.05 by Student's t-test for all samples (N=3). Without either UV irradiation or 5-FC addition, little toxicity was observed. Interestingly, this same trend was found at all the enzyme incubation time points, even 48 h after adding the affibody-enzymes to the MDA-MB-468 cells. Thus, this affibody-enzyme photocrosslinking strategy holds promise for longer-term retention of pro-drug activation by prolonging the expression and lifetime of the affibody-enzymes on the cell membrane.

This work shows the possibility of using a direct affinity-mediated covalent chemistry approach to tag receptors on live cells with unique protein segments while retaining expression over many days without genetic engineering. This result was shown by first synthesizing an affibody-CodA construct that could form covalent photocrosslinks with EGFR through coupling of an attached benzophenone. Flow cytometry measurements showed that affibody-enzymes photocrosslinked to EGFR on live MDA-MB-468 cells were first internalized, but then were recycled outside of endosomal compartment and back to the cell membrane. Without photoconjugation, WT affibody-enzymes showed internalization followed by rapid proteolysis. In addition, confocal microscopy images revealed high colocalization of dually-dye-labeled affibody-enzyme fusion proteins, showing the fidelity of the protein structure during and after internalization by the cell. Finally, photocrosslinkable affibody-enzyme proteins were found to function as effective agents for prodrug therapy even two days after crosslinking, as shown by continued prodrug activation and cell killing. In contrast, the WT affibody-enzyme proteins showed minimal cell killing even after only 8 h of incubation with cells. Thus, while non-photocrosslinked fusion proteins are internalized and eventually proteolyzed by the cell, covalently conjugating the N23-CodA to EGFR enables the fusion protein to successfully evade degradation.

The reported work may both improve upon cancer therapies and expand the cell bioconjugation toolkit. First, a major limitation of antibody-directed enzyme prodrug therapy is that enzyme activity is lost at the tumor site after endocytosis and proteolysis by the cancer cells. In this work, by covalently conjugating the enzyme to a cell receptor to prevent dissociation, the enzyme is able to return to the cell surface as a result of receptor recycling. As a result, prodrug conversion was shown days after adding the targeted enzyme to cells. As opposed to non-covalent association, covalently conjugating the fusion protein appears to mask its presence to the cell. Thus, as the EGFR is recycled back to the membrane, the fusion protein goes along for the ride, escaping the harsh environment of the endosome and lysosome. More broadly, photocrosslinking proteins to membrane proteins results in their display on cell surfaces for any application requiring modification of cell receptors without modifying genetic machinery of the cell.

Materials and Methods

Figure 23:
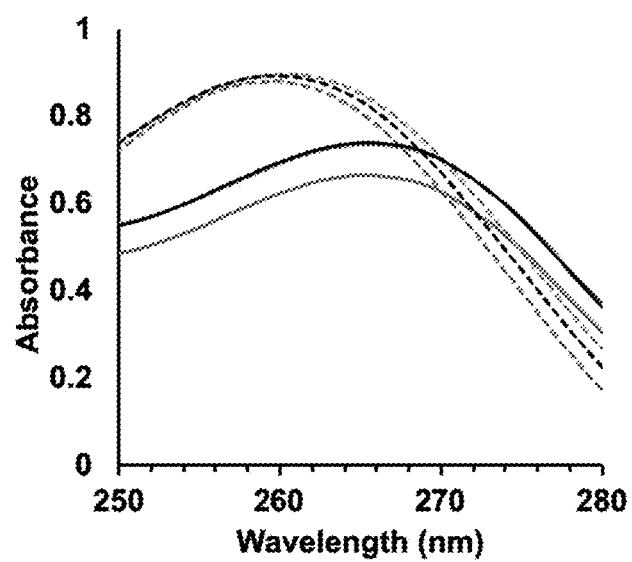
FIG. 23 is a graph depicting the absorbance spectra showing the conversion of cytosine (267 nm) to uracil (260 nm) before (solid) and 15 min after addition (dotted lines) of 50 nM N23BP-CodA (blue), WT-CodA (orange), and CodA (black) to 200 µM of cytosine.
Figure 24:
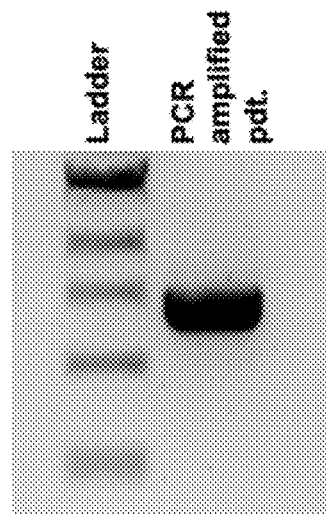
FIG. 24 is an of image showing that CodA gene (1.2 kbp) successfully amplified from $E.\ coli$ BL21(DE3) strain by PCR amplification. Ladder proteins are (top to bottom) 3, 2, 1.5, 1.0 and 0.5 kbp.
Figure 25:
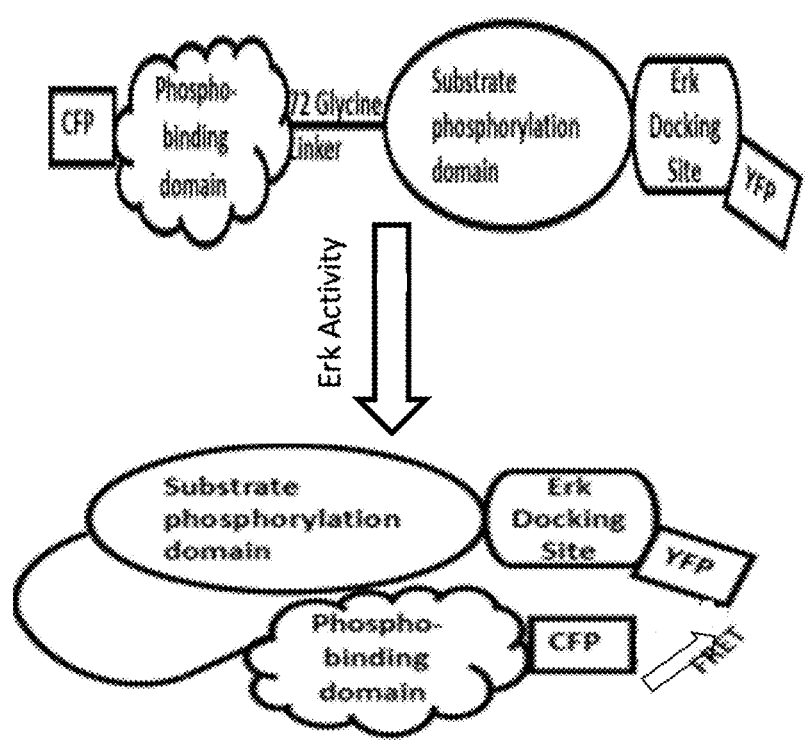
FIG. 25 is a diagram depicting the schematic of the EKAR sensor. The ERK phosphorylation brings about a conformational change in the structure that result in the FRET.

Amplification of CodA Gene: *E. coli* strain BL21(DE3) was used as the template for amplifying CodA gene encoded for cytosine deaminase. The sequence for the forward and the reverse primers (NEB) were 5'-aagcttGGCGGTGGCTCGAATAACCTTTA-CAAACAATTATTAAC-3' [SEQ ID NO. 1] and 3'-ctcga-gACGTTTGTAATCGATGGCTTCT-5' [SEQ ID NO. 2], where the underlined regions are the annealing nucleotides. The primers incorporate a HindIII site at the 5' position and an XhoI site at the 3' position of the amplified sequence. The amplification was done using a standard PCR technique (Applied Biosystems, Gene Amp, PCR systems 9700) where primers were annealed at 65° C. (FIG. 23).

Expression, Synthesis, and Purification of Affibody-enzyme Fusion Proteins: The codon sequence for WT and N23C affibody (in vector Pet21b+) was digested for 1 h at 37° C. using the restriction enzymes HindIII and XhoI. The two plasmids (amplified CodA and the digested WT and N23C) were ligated using a standard ligation mixture supplied by NEB. *E. coli* BL21 (DE3) was made competent using an Eppendorf Eporator (4309000019) at 1300 V, followed by transformation of the ligated plasmid. The transformed *E. coli* were then grown on an ampicillin (selection marker) coated agar plate overnight.

A single colony from the overnight plate was picked and suspended in 5 mL Luria Broth (LB) supplemented with 5 μL ampicillin and allowed to grow for 12 h. 500 μL of this culture was then transferred to 50 mL of LB supplemented with 50 μL of ampicillin and allowed to grow for 2 h, after which the OD600 of the culture was measured. At OD 0.7, 50 μL of the inducer solution 1 M isopropyl β-D-1 thiogalactopyranoside (IPTG, GoldBio) was added. The culture was allowed to grow further for 3 more hours, after which the culture was centrifuged (10000 g for 5 min), and the supernatant discarded. The bacterial pellet from this culture was then resuspended in 25 mL equilibration buffer (5 mM imidazole in water) and sonicated at 25% power (1 min and 1 min off, total on: 4 min) to lyse the pellets (Branson Ultrasonic Cell Disruptor). The lysed cells were then centrifuged (12000 g for 20 min) and 200 μL of HisPur Ni-NTA suspension (Thermo Fisher) was added to the lysate and incubated for 1 h at RT on a rotisserie shaker. The Ni-NTA beads were then centrifuged (700 g for 2 min) and washed 5× with a wash buffer (25 mM imidazole in water) and finally the adsorbed fusion affibodies were eluted by incubating the elution buffer (250 mM imidazole in water) with the beads for 10-15 min on a rotisserie shaker.

The concentrations of the newly purified affibody-enzyme fusions were measured using a Nanodrop Lite Spectrophotometer (Thermo Fisher), then reacted with 20:1 molar excess of 4-N-maleimido benzophenone (VWR) overnight in the dark at RT. Excess benzophenone and imidazole were removed using 20k MWCO Zeba spin desalting columns (Life Technologies) and the final affibody-enzyme fusion concentration was measured by UV-Vis spectroscopy. The purified fusion affibodie-enzymes were then stored at −20° C. in 10 μL aliquots with 5% glycerol. 10 μL of the purified fusion affibody-enzymes were then denatured with 2% w/w SDS and heating for 10 min at 70° C. in a thermocycler (GeneAmp PCR Systems 9700, Applied Biosystem). The samples were then loaded into polyacrylamide gel (Thermo Fisher) and electrophoresed for 35 min at 200V in MES running buffer (50 mM MES, 50 mM Tris base, 1% SDS, 1 mM EDTA). The gel was washed thrice in boiling water, followed by staining with Coomassie (Simply Blue Stain, Thermo Fisher). The gels were then imaged with Typhoon FLA 9500 scanner to check for sample purity.

Microscale Thermophoresis (MST) Measurements: Extracellular domain of purified human EGFR (Sino Biologics) was conjugated to NHS-AF647 (Thermo Fisher) in 10:1 ratio. The excess dye was removed using 20k MWCO dialysis cups (Thermo Fisher), leading to a final degree of labeling of 1:1. Labeled AF647-EGFR was then mixed with sixteen different concentrations (50 μM to 100 μM) of unlabeled N23-CodA and WT-CodA affibody-enzymes in PBS with 0.05% Tween in Low-Adhesion Microcentrifuge Tubes (Genemate). The mixtures were then loaded onto micro-capillaries (NanoTemper, Monolith NT.115 Series) and the signal from each were measured using the MST instrument (NanoTemper). The signals were then fit to a binding model using the instrument software to obtain respective Kd values.

Photocrosslinking of Affibody-enzyme fusions with EGFR: 200 nM of purified human extracellular EGFR (Sino Biological) was mixed with 5 μM of N23-CodA and WT-CodA affibody-enzymes in a microcentrifuge tube and irradiated with 890 μW/cm$^2$ 365 nm light for 30 min. The mixtures were then deglycosylated with PNGase F for 2 h at 37° C. The samples were denatured with 2% w/v SDS and heated at 70° C. for 10 min. The samples were then loaded onto 4-12% Bis-Tris polyacrylamide gels (Thermo Fisher) and electrophoresed for 35 min at 200 V in MES running buffer (50 mM MES, 50 mM Tris base, 1% SDS, 1 mM EDTA). The gel was washed thrice in boiling water, followed by staining with Coomassie (Simply Blue Stain, Thermo Fisher). The gels were then imaged with Typhoon FLA 9500 scanner to check for the photo-crosslinked products.

Circular Dichroism (CD) Measurements: Affibody-enzymes were diluted to 10 μM in PBS and measurements were obtained at 222 nm as temperature was raised from 20 to 90° C. at 1° C./min in an Applied Photophysics Chirascan Plus CD instrument. Temperature inside the cuvette was monitored using a thermocouple probe.

Affibody-enzyme Kinetic Activity Assays with Cytosine: The enzymatic assay for N23-CodA, WT-CodA, and CodA were performed by varying substrate concentration and measuring the absorbance using a UV-VIS spectrophotometer (Agilent Technologies, Cary Series 100). A stock of 10 mM cytosine was prepared in 50 mM Tris-HCl at pH 7.5. Varying concentrations (250, 200, 150 and 100 μM) of cytosine solution were prepared from the stock and mixed with 50 nM of the enzyme and enzyme-affibodies. The reaction was run for 15 min with $OD_{267}$ (cytosine) and $OD_{260}$ (uracil) readings taken every 12 s. The concentration of cytosine was calculated for each time point and the kinetic parameters $K_M$ and $k_{cat}$ were calculated using the methods of initial rates and double reciprocal plots.

Conjugation of AlexaFluor 488 (AF488) and pHAb to affibody-enzymes: The affibody-enzymes (N23-CodA and WT-CodA) were conjugated to 1:10 molar excess NHS-AlexaFluor 488 (Thermo Fisher) and the pH-sensitive NHS-pHAb (Promega) in separate tubes for 2 h at RT in the dark in PBS. The mixtures were then transferred to a 20k MWCO dialysis cups (Thermo Fisher) and excess dye was removed by dialysis. After 36 h dialysis, the degree of labeling for both the dye-conjugated affibody fusions were calculated using UV-Vis spectrophotometry (Agilent Technologies, Cary Series 100), by using the absorbance at 545 nm for the endotracker pHAb and 495 nm for AF488 as compared to the absorbance at 280 nm for both affibody-fusions.

Flow Cytometry Measurements: MDA-MB-468 cells were grown to confluence at 37° C. under 5% $CO_2$. The cells were trypsinized with 0.025% Trypsin-EDTA (Gibco) and 500 μL of the cell suspension was seeded at 25,000 cells per well in 24-well cell culture plates (Corning). The cells were then allowed to grow in the wells for 36 h at 37° C. and 5% $CO_2$. The media was then removed and the cells were washed with PBS. The cells were then incubated with 1 μM AF488-conjugated affibody-enzymes and pHAb-conjugated affibody-enzymes separately in media for 2, 4, 6, 12, and 24 h. After 3 h, the wells were irradiated with 890 μW/cm$^2$ 365 nm light for 30 min, after which the wells were placed back in the incubator. At each timepoint, the media was removed and the cells were washed thrice to remove excess dye-conjugated affibody-enzymes. The cells were then trypsinized with 0.025% Trypsin-EDTA (Gibco) and fixed with 4% paraformaldehyde. Before flow cytometry, the paraformaldehyde solution was removed and the cells were resuspended in DPBS. The fluorescence from the cells was measured using BD FACSCelesta instrument (BD Biosciences). For measurement of AF488 fluorescence, a 488 nm laser was used, while for measuring the phAb fluorescence a 561 nm laser was used. The raw data was then analyzed using Flowing Software (OmicX).

Culture of MDA-MB-468 Breast Cancer Cells: MDA-MB-468 breast carcinoma cells were procured from the American Type Culture Collection (ATCC) and grown in 75 cm$^2$ culture flasks at 37° C. under 5% $CO_2$ in the presence of Dulbecco's Modified Eagle Media (DMEM, with glucose and glutamine, phenol red but no sodium pyruvate, Gibco) supplemented with 10% fetal bovine serum (FBS, Gibco) and 1% penicillin-streptomycin (Thermo Fisher).

Confocal Microscopy: MDA-MB-468 cells were grown to confluence at 37° C. under 5% $CO_2$. The cells were trypsinized with 0.025% Trypsin-EDTA (Gibco) and 500 μL of the cell suspension was seeded at 20,000 cells per well in 24-well cell culture plates (Corning) with a poly-L-lysine coated glass coverslip (Corning BioCoat) already placed in each well. The cells were then allowed to grow in the wells for 36 h at 37° C. and 5% $CO_2$, after which the media was removed and the cells were washed with PBS. The cells were then incubated with 1 µM AF488-conjugated affibody-enzymes (both N23-CodA and WT-CodA) and pHAb-conjugated affibody-enzymes (N23-CodA and WT-CodA) separately in media for 4, 12 and 24 h. After 3 h, the wells were irradiated with 890 µW/cm²365 nm light for 30 min, after which the wells were placed back in the incubator. After each time point, the media was removed, and the cells were washed with PBS to remove excess dye-affibody enzymes. The cells were then incubated with 1 µg/mL of 4',6-diamidino-2-phenylindole (DAPI) for 10 min to stain the cell nucleus. The cells were again washed thrice with PBS. The cells were then mounted with ProLong Antifade agent (Thermo Fisher) on a glass slide and imaged with a Nikon AiR Laser Confocal Microscope.

Prodrug Cytotoxicity (MTT) Assays: The MDA-MB-468 cells were grown to confluence, after which the cells were washed once with DPBS (Gibco) and then trypsinized with 0.025% trypsin-EDTA (Gibco). 200 µL of the cell suspension in media was seeded in 96-well cell culture plates (Corning) at density of 2000 cells/well. The cells were then grown for 24 h at 37° C. under 5% CO2. The N23-CodA and WT-CodA affibody-enzymes and CodA enzyme itself were diluted in DMEM to a final conc. of 1 µM. After removal of old media from the wells, 100 µL of the appropriate protein solution (N23CodA, WT-CodA, CodA, or no protein) was added. The cells were then incubated at 37° C. under 5% CO2 with the enzyme/affibody-enzyme. After 3 h, cells were irradiated with 890 µW/cm2 of 365 nm light for 30 min. For the (−)UV controls, cells were not irradiated with UV. When the timepoint was reached (8, 24, or 48 h after introducing the protein), the cells were washed thrice with PBS to remove any excess enzyme/affibody-enzyme. Next, 100 µL of 2 mM 5-FC was added to each well, while for control wells 100 µL was added instead. To measure the effect of 5-FC and 5-FU on cells, some wells were treated with only 5-FC and just 5-FU, without any protein. Excess 5-FC was removed after 12 h and the cells were washed with PBS and 100 µL of 1 mg/mL (3-(4,5-dimethylthiazol-2-yl)-2,5-diphenyl tetrazolium bromide) (MTT) in media was added to each of the wells. After 4 h, the media was removed from each well carefully to avoid disturbing the formazan crystals at the bottom. The crystals were dissolved in 100 µL isopropyl alcohol (IPA), and absorbance from the wells was measured at 570 nm in a Tecan Safire II Multimode Plate reader. The readings were then normalized to the cells that were treated with neither enzyme, enzyme-affibody, nor 5-FC/5-FU to calculate the fractional viability. All experiments were performed in triplicate.

DEFINITIONS AND ABBREVIATIONS

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "and/or" whereever used herein includes the meaning of "and", "or" and "all or any other combination of the elements connected by said term".

The term "about" or "approximately" as used herein means within 20%, preferably within 10%, and more preferably within 5% of a given value or range.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

Affibody molecules are affinity proteins with specific affinities to target proteins, such as cell surface receptors. Affibody molecules have demonstrated effectiveness in therapeutic, diagnostic and biotechnological applications. Affibody molecules are generally small (in the range of 6.5 kDa) single domain proteins that can be isolated for high affinity and specificity to any given protein target.

A prodrug is a biologically inactive compound which can be metabolized in the body to produce a drug. Instead of administering a drug directly, a corresponding prodrug can be used to improve how the drug is absorbed, distributed, metabolized, and excreted.

The term "administration" and variants thereof (e.g., "administering" a compound, "administering" a prodrug, "administering" an affibody-prodrug enzyme fusion polypeptide) in reference to a compound of the invention means introducing the compound into the system of the subject in need of treatment. When a compound of the invention is provided in combination with one or more other active agents or prodrugs (e.g., a cytotoxic agent, etc.), "administration" and its variants are each understood to include concurrent and sequential introduction of the compound and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound (e.g. an affibody-prodrug enzyme fusion polypeptide) or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation or metastasis of the tumor. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

As used herein, "treatment" refers to obtaining beneficial or desired clinical results. Beneficial or desired clinical results include, but are not limited to, any one or more of: alleviation of one or more symptoms (such as tumor growth or metastasis), diminishment of extent of cancer, stabilized (i.e., not worsening) state of cancer, preventing or delaying spread (e.g., metastasis) of the cancer, preventing or delaying occurrence or recurrence of cancer, delay or slowing of cancer progression, amelioration of the cancer state, and remission (whether partial or total). The methods of the invention contemplate any one or more of these aspects of treatment.

A "subject in need of treatment" is a mammal with cancer or other medical condition that is life-threatening or that impairs health or shortens the lifespan of the mammal.

A "pharmaceutically acceptable" component is one that is suitable for use with humans and/or animals without undue adverse side effects (such as toxicity, irritation, and allergic response) commensurate with a reasonable benefit/risk ratio.

A "safe and effective amount" refers to the quantity of a component that is sufficient to yield a desired therapeutic response without undue adverse side effects (such as toxicity, irritation, or allergic response) commensurate with a reasonable benefit/risk ratio when used in the manner of this invention.

As used herein, the term "pretreating", or "pretreatment", is intended to mean that a first treatment is administered prior to, or in conjunction with, a second treatment. In other words, the pretreatment may be performed before another, later treatment, thus allowing the pretreatment time to take effect. Alternatively, the pretreatment may be performed or administered simultaneously with a second treatment without a temporal delay. Advantageously, a pretreatment is administered prior to a second treatment. It is envisioned that pretreatment with an affibody-prodrug enzyme fusion polypeptide can be performed 1 hr., 2 hrs., 4 hrs., 8 hrs., 1 day, 2 days, 4 days, or 1 week prior to treatment with a drug or prodrug.

Kits for practicing the methods of the invention are further provided. By "kit" is intended any manufacture (e.g., a package or a container) comprising at least one reagent, e.g., a pH buffer of the invention. The kit may be promoted, distributed, or sold as a unit for performing the methods of the present invention. Additionally, the kits may contain a package insert describing the kit and methods for its use. Any or all of the kit reagents may be provided within containers that protect them from the external environment, such as in sealed containers or pouches.

In an advantageous embodiment, the kit containers may further include a pharmaceutically acceptable carrier. The kit may further include a sterile diluent, which is preferably stored in a separate additional container. In another embodiment, the kit further comprising a package insert comprising printed instructions directing the use of a combined treatment of an pH buffer and the anti-cancer agent as a method for treating tumors, tumor metastases, or other cancers in a patient. The kit may also comprise additional containers comprising additional anti-cancer agents, agents that enhances the effect of such agents, or other compounds that improve the efficacy or tolerability of the treatment.

As used herein, the terms "patient" or "subject" preferably refers to a human in need of treatment with an anti-cancer agent or treatment for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an anti-cancer agent or treatment.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

The anti-cancer agent or treatment will typically be administered to the patient in a dose regimen that provides for the most effective treatment of the cancer (from both efficacy and safety perspectives) for which the patient is being treated, as known in the art. In conducting the treatment method of the present invention, the anti-cancer agent or treatment can be administered in any effective manner known in the art, such as by oral, topical, intravenous, intra-peritoneal, intramuscular, intra-articular, subcutaneous, intranasal, intra-ocular, vaginal, rectal, or intradermal routes, depending upon the type of cancer being treated, the type of anti-cancer agent or treatment being used, and the medical judgment of the prescribing physician as based, e.g., on the results of published clinical studies.

Abbreviations used herein:

5-FC, 5-fluorocytosine; 5-FU, 5-fluorouracil; BP, benzophenone; CodA, cytosine deaminase; DAPI, 4',6-diamidino-2-phenylindole; DNA, deoxyribonucleic acid; EGF, epidermal growth factor; EGFR, epidermal growth factor receptor; FcRn, neonatal Fc receptor; IgG, immunoglobulin G; KD, dissociation constant; KM, Michaelis-Menten constant; MST, microscale thermophoresis; MWCO, molecular weight cutoff; Ni-NTA, nickel nitrilotriacetic acid; NIR, near infrared; PCC, Pearson Correlation Coefficient; PCR, polymerase chain reaction; SDS-PAGE, sodium dodecylsulfate polyacrylamide gel electrophoresis; UV, ultraviolet; WT, wildtype.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

All references cited in the present application are incorporated in their entirety herein by reference to the extent not inconsistent herewith.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

TABLE S1

Kinetic data for different enzyme fusion proteins.

|  | CodA | N23BP-CodA | WT-CodA |
|---|---|---|---|
| Km (mM) | 2.52 | 2.20 | 1.74 |
| kcat (s$^{-1}$) | 53.57 | 45.98 | 48.58 |
| kcat/Km (mM$^{-1}$ s$^{-1}$) | 21.23 | 20.89 | 27.90 | contacting the cell with a prodrug following the photoconjugating step, whereby the prodrug enzyme portion of the fusion protein converts the prodrug to the active form of the drug upon contact of the prodrug with the cell.

5. The method of presenting a prodrug enzyme on a cell surface according to claim 2 wherein the cell is a breast cancer cell.

6. The method of presenting a prodrug enzyme on a cell surface according to claim 2 wherein the photoconjugation is performed using long UV or NIR light in the presence of upconverting nanoparticles.

7. A fusion protein comprising an N23C mutated $Z_{EGFR:1907}$ affibody and cytosine deaminase, wherein the affibody has a benzophenone group conjugated to this cysteine, whereby the benzophenone group facilitates conjugation to an epidermal growth factor receptor (EGFR) on a target cell.

8. A method of presenting an enzyme on a cell surface comprising the steps of:
   contacting a cell with a fusion protein according to claim 7;
   photoconjugating the fusion protein to the surface of the cell; and
   contacting the cell with a prodrug following the photoconjugating step, whereby the cytosine deaminase con-

What is claimed is:

1. A fusion protein comprising a prodrug enzyme and an N23C mutated $Z_{EGFR:1907}$ affibody having a benzophenone group conjugated to this cysteine.

2. A method of presenting a prodrug enzyme on a cell surface comprising the steps of:
   contacting the cell with a fusion protein according to claim 1; and
   photoconjugating the fusion protein to the surface of the cell by photoirradiation of the cell.

3. The method of presenting a prodrug enzyme on a cell surface according to claim 2 wherein the photoconjugating is performed by photoirradiation of the cell with either long UV or NIR light.

4. The method of presenting a prodrug enzyme on a cell surface according to claim 2 further comprising the step of verts the prodrug to the active form of the drug upon contact of the prodrug with the cell.

9. The method of presenting an enzyme on a cell surface according to claim 8 wherein the cell is a breast cancer cell.

10. The method of presenting an enzyme on a cell surface according to claim 8 wherein the prodrug is 5-fluorocytosine (5-FC).

11. A method to modify a cell receptor of a target cell with a unique biological tag comprising the steps of:
   contacting a cell with a fusion protein comprising a $Z_{EGFR:1907}$ affibody fused to a peptide desired to be presented on a cell surface, wherein the affibody has an N23C mutation and has a benzophenone group conjugated to this cysteine;
   and photoconjugating the fusion protein to the surface of the cell.

12. The method to modify a cell receptor of a target cell with a unique biological tag according to claim 11 wherein the photoconjugation is performed using long UV or NIR light in the presence of upconverting nanoparticles.

13. A fusion protein comprising a polypeptide desired to be presented on a cell surface linked to a $Z_{EGFR:1907}$ affibody having an N23C mutation, wherein a benzophenone group is conjugated to this cysteine.

14. The fusion protein according to claim 13 wherein the polypeptide is an enzyme.

15. A method of presenting an enzyme on a cell surface comprising the steps of:
 contacting the cell with the fusion protein according to claim 14; and
 photoconjugating the fusion protein to the surface of the cell by photoirradiation of the cell, wherein the photoconjugation is performed using long UV or NIR light in the presence of upconverting nanoparticles.

16. The method of presenting an enzyme on a cell surface according to claim 15 wherein the enzyme is cytosine deaminase.

\* \* \* \* \*